(12) United States Patent
Donde et al.

(10) Patent No.: US 7,713,968 B2
(45) Date of Patent: May 11, 2010

(54) SUBSTITUTED ARYLCYCLOPENTENES AS THERAPEUTIC AGENTS

(75) Inventors: Yariv Donde, Dana Point, CA (US); Jeremiah H. Nguyen, La Puente, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 12/427,860

(22) Filed: Apr. 22, 2009

(65) Prior Publication Data

US 2009/0270387 A1 Oct. 29, 2009

Related U.S. Application Data

(60) Provisional application No. 61/047,599, filed on Apr. 24, 2008.

(51) Int. Cl.
| | |
|---|---|
| A61K 31/341 | (2006.01) |
| A61K 31/381 | (2006.01) |
| A61K 31/421 | (2006.01) |
| A61K 31/426 | (2006.01) |
| A61K 31/5377 | (2006.01) |
| A61K 31/5575 | (2006.01) |
| C07D 265/30 | (2006.01) |
| C07D 236/32 | (2006.01) |
| C07D 277/22 | (2006.01) |
| C07D 333/10 | (2006.01) |
| C07D 307/40 | (2006.01) |
| C07C 69/74 | (2006.01) |

(52) U.S. Cl. .............. 514/231.5; 514/238.8; 514/448; 514/461; 514/365; 514/374; 514/880; 514/530; 544/106; 548/201; 548/235; 549/71; 549/484; 560/122

(58) Field of Classification Search ............ 514/231.5, 514/238.8, 448, 461, 365, 374, 880, 530; 548/201, 235; 544/106; 549/71, 484; 560/122
See application file for complete search history.

(56) References Cited

U.S. PATENT DOCUMENTS

| | | | |
|---|---|---|---|
| 5,462,968 | A | 10/1995 | Woodward |
| 5,698,598 | A | 12/1997 | Woodward |
| 6,090,847 | A | 7/2000 | Woodward |
| 6,437,146 | B1 | 8/2002 | Hattori |
| 6,710,072 | B2 | 3/2004 | Burk |
| 7,091,231 | B2 | 8/2006 | Donde |

FOREIGN PATENT DOCUMENTS

| | | |
|---|---|---|
| EP | 0308135 | 3/1989 |
| WO | WO 93/14743 | 8/1993 |
| WO | WO 2007/131012 | 11/2007 |
| WO | WO 2008/091818 | 7/2008 |
| WO | WO 2008/094912 | 8/2008 |

OTHER PUBLICATIONS

Carey, Francis A.: Conformations of Alkanes and Cycloalkanes. Organic Chemistry, New York: McGraw-Hill Book Company 1987, p. 63.

Furrow, M.E.; Myers, A.G.: Practical Procedures for the Preparation of N-tert-Butyldimethylsilylhydrazones and Their Use in Modified Wolff-Kishner Reductions and in the Synthesis of Vinyl Halides and gem-Dihalides. J. Am. Chem. Soc. 2004, 126, 5436.

Resul, B.; et al.: Structure-Activity Relationships of Prostaglandin Analogues as Ocular Hypotensive Agents. Current Opinon in Therapeutic Patents, vol. 3, No. 6, Jan. 1, 1993, pp. 781-795.

*Primary Examiner*—Kamal A Saeed
*Assistant Examiner*—Michael Barker
(74) *Attorney, Agent, or Firm*—Kevin J. Forrestal; John E. Wurst; Allergan, Inc.

(57) ABSTRACT

Compounds comprising

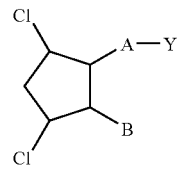

or a pharmaceutically acceptable salt or a prodrug thereof, are disclosed, wherein Y, A, and B are as described.

Methods, compositions, and medicaments related thereto are also disclosed.

12 Claims, No Drawings

SUBSTITUTED ARYLCYCLOPENTENES AS THERAPEUTIC AGENTS

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

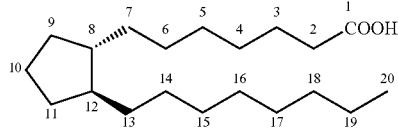

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

The prostaglandin E analog shown below is disclosed in the following documents, expressly incorporated herein by reference: U.S. Pat. No. 5,462,968; U.S. Pat. No. 5,698,598; and U.S. Pat. No. 6,090,847.

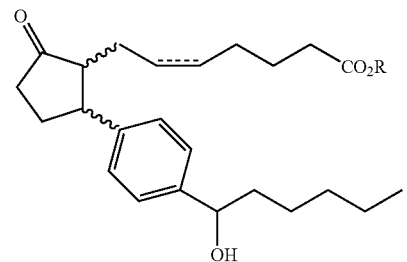

Other $EP_2$ selective agonists are disclosed in U.S. patent application Ser. No. 11/009,298, filed Dec. 10, 2004 (now U.S. Pat. No. 7,091,231 issued Aug. 15, 2006). Prostaglandin $EP_2$ selective agonists are believed to have several medical uses. For example, U.S. Pat. No. 6,437,146 teaches the use of prostaglandin $EP_2$ selective agonists "for treating or preventing inflammation and pain in joint and muscle (e.g., rheumatoid arthritis, rheumatoid spondylitis, osteoarthritis, gouty arthritis, juvenile arthritis, etc.), inflammatory skin condition (e.g., sunburn, burns, eczema, dermatitis, etc.), inflammatory eye condition (e.g., conjunctivitis, etc.), lung disorder in which inflammation is involved (e.g., asthma, bronchitis, pigeon fancier's disease, farmer's lung, etc.), condition of the gastrointestinal tract associated with inflammation (e.g., aphthous ulcer, Chrohn's disease, atrophic gastritis, gastritis varialoforme, ulcerative colitis, coeliac disease, regional ileitis, irritable bowel syndrome, etc.), gingivitis, inflammation, pain and tumescence after operation or injury, pyrexia, pain and other conditions associated with inflammation, allergic disease, systemic lupus crythematosus, scleroderma, polymyositis, tendinitis, bursitis, periarteritis nodose, rheumatic fever, Sjgren's syndrome, Behcet disease, thyroiditis, type I diabetes, diabetic complication (diabetic microangiopathy, diabetic retinopathy, diabetic neohropathy, etc.), nephrotic syndrome, aplastic anemia, myasthenia gravis, uveitis contact dermatitis, psoriasis, Kawasaki disease, sarcoidosis, Hodgkin's disease, Alzheimers disease, kidney dysfunction (nephritis, nephritic syndrome, etc.), liver dysfunction (hepatitis, cirrhosis, etc.), gastrointestinal dysfunction (diarrhea, inflammatory bowel disease, etc.) shock, bone disease characterized by abnormal bone metabolism such as osteoporosis (especially, postmenopausal osteoporosis), hypercalcemia, hyperparathyroidism, Paget's bone diseases, osteolysis, hypercalcemia of malignancy with or without bone metastases, rheumatoid arthritis, periodonritis, osteoarthritis, ostealgia, osteopenia, cancer cachexia, calculosis, lithiasis (especially, urolithiasis), solid carcinoma, mesangial proliferative glomerulonephritis, edema (e.g. cardiac edema, cerebral edema, etc.), hypertension such as malignant hypertension or the like, premenstrual tension, urinary calculus, oliguria such as the one caused by acute or chronic failure, hyperphosphaturia, or the like."

U.S. Pat. No. 6,710,072 teaches the use of EP2 agonists for the treatment or prevention of "osteoporosis, constipation, renal disorders, sexual dysfunction, baldness, diabetes, cancer and in disorder of immune regulation . . . various pathophysiological diseases including acute myocardial infarction, vascular thrombosis, hypertension, pulmonary hypertension, ischemic heart disease, congestive heart failure, and angina pectoris."

SUMMARY OF THE INVENTION

Disclosed herein are compounds useful in treating glaucoma, inflammatory bowel disease, the stimulation of hair growth, and the stimulation of the conversion of vellus hair to terminal hair. The compounds themselves are disclosed below.

DESCRIPTION OF THE INVENTION

Disclosed herein is a compound of the formula

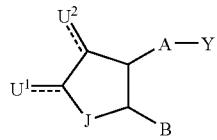

or a pharmaceutically acceptable salt thereof, or a prodrug thereof;

wherein a dashed line represents the presence or absence of a bond;

Y is

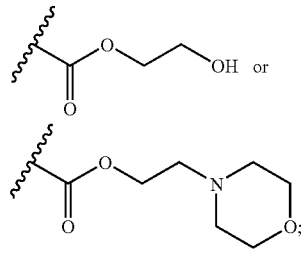

A is —$(CH_2)_6$—, cis —$CH_2CH=CH$—$(CH_2)_3$—, or —$CH_2C\equiv C$—$(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein 1 —$CH_2$— may be replaced by S or O, and 1 —$CH_2$—$CH_2$ may be replaced by —CH=CH— or C≡C;

$U^1$ and $U^2$ are independently H, O; OH, I, Br, Cl, F, $CF_3$, CN, or $CH_2OH$;

J is

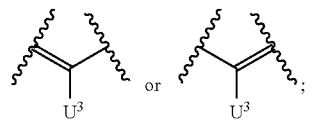

$U^3$ is H, OH, I, Br, Cl, F, CN, $C_{1-6}$ alkyl, aryl, heteroaryl, or $C_{1-6}$ hydroxyalkyl; and B is aryl or heteroaryl.

These compounds are useful for treating glaucoma or ocular hypertension.

The definitions, explanations, and examples provided in this document shall be used to determine the meaning of a particular term or expression where there is any ambiguity arising from any disclosure incorporated by reference herein.

A is —$(CH_2)_6$—, cis —$CH_2CH=CH$—$(CH_2)_3$—, or —$CH_2C\equiv C$—$(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein 1 —$CH_2$— may be replaced by S or O, and 1 —$CH_2$—$CH_2$ may be replaced by —CH=CH— or C≡C—.

Thus, while not intending to be limiting, A may be —$(CH_2)_6$—, cis —$CH_2CH=CH$—$(CH_2)_3$—, or —$CH_2C\equiv C$—$(CH_2)_3$—.

Alternatively, A may be a group which is related to one of these three moieties in that any carbon is replaced with S or O. For example, while not intending to limit the scope of the invention in any way, A may be a moiety where S replaces one or two carbon atoms such as one of the following or the like.

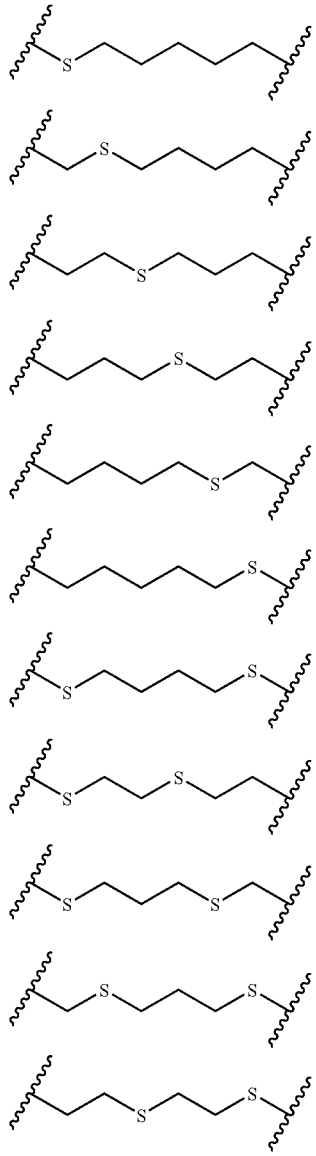

-continued

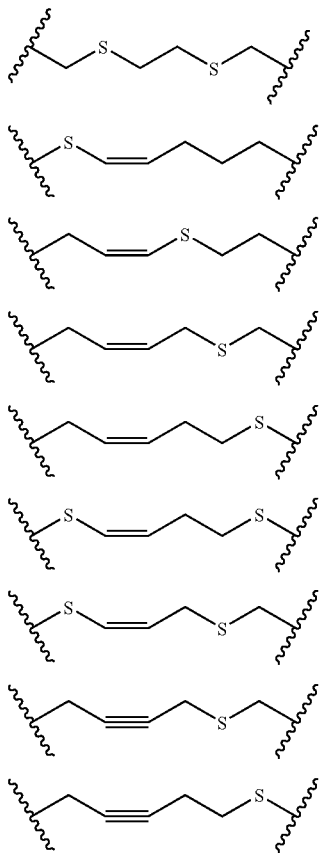

Alternatively, while not intending to limit the scope of the invention in any way, A may be a moiety where O replaces one or two carbon atoms such as one of the following or the like.

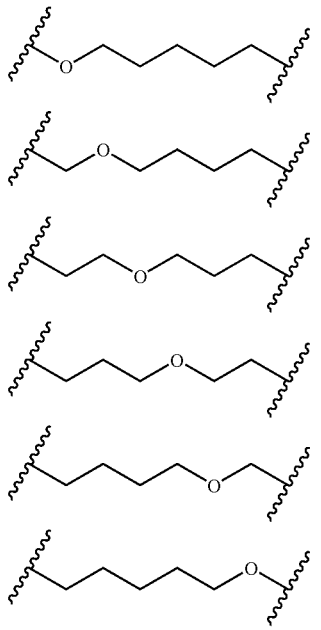

-continued

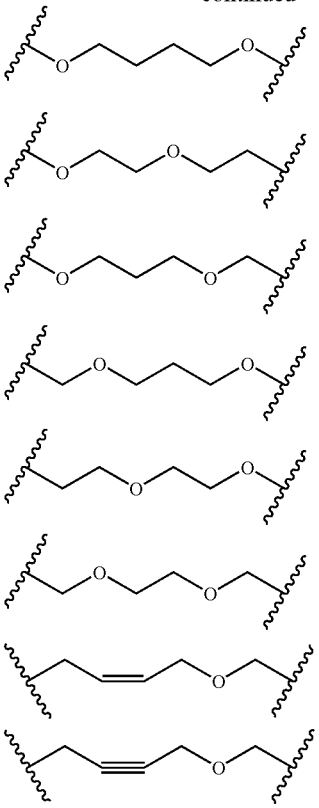

Alternatively, while not intending to limit the scope of the invention in any way, A may have an O replacing one carbon atom and an S replacing another carbon atom, such as one of the following or the like.

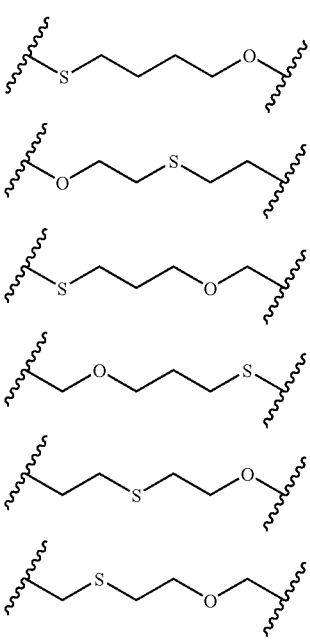

Alternatively, while not intending to limit the scope of the invention in any way, in certain embodiments A is —(CH$_2$)

$_m$—Ar—(CH$_2$)$_o$— wherein Ar is interarylene or heterointerarylene, the sum of m and o is 1, 2, 3, or 4, and wherein 1 —CH$_2$— may be replaced by S or O, and 1 —CH$_2$—CH$_2$ may be replaced by —CH=CH— or —C≡C—. In other words, while not intending to limit the scope of the invention in any way, n one embodiment A comprises:
1) a) 1, 2, 3, or 4 CH$_2$ moieties, or
   b) 0, 1 or 2 CH$_2$ moieties and —CH=CH— or —C≡C—; and
2) Ar;
e.g. —CH$_2$—Ar—, —(CH$_2$)$_2$—Ar—, —CH=CH—Ar—, C≡C—Ar—, —CH$_2$—Ar—CH$_2$—, —CH$_2$Ar—(CH$_2$)$_2$—, —CH$_2$Ar—CH=CH—, —CH$_2$Ar—C≡C—, —(CH$_2$)$_2$—Ar—(CH$_2$)$_2$—, and the like;

in another embodiment A comprises:
1) a) O; and 0, 1, 2, or 3 CH$_2$ moieties; or
   b) O; and 0 or 1 CH$_2$ moieties and —CH=CH— or —C≡C—; and
2) Ar;
e.g., —O—Ar—, Ar—CH$_2$—O—, —O—Ar—(CH$_2$)$_2$—, —OAr—CH=CH—, —O—Ar—C≡C—, —O—CH$_2$—Ar—, —O—CH$_2$—Ar—(CH$_2$)$_2$, —O—CH$_2$Ar—CH=CH—, —O—CH$_2$Ar—C≡C—, and the like; or in another embodiment A comprises:
1) a) S; and 0, 1, 2, or 3 CH$_2$ moieties; or
   b) S; and 0 or 1 CH$_2$ moieties and —CH=CH— or —C≡C—; and
2) Ar;
e.g., —S—Ar—, Ar—CH$_2$—S—, —S—Ar—(CH$_2$)$_2$—, —SAr—CH=CH—, —S—Ar—C≡C—, —S—CH$_2$—Ar—, —S—CH$_2$—Ar—(CH$_2$)$_2$, —S—CH$_2$Ar—CH=CH—, —S—CH$_2$Ar—C≡C—, and the like.

In another embodiment, the sum of m and o is 2, 3, or 4 wherein one CH$_2$ may be replaced with S or O and 1 —CH$_2$—CH$_2$ may be replaced by —CH=CH— or —C≡C—.

In another embodiment, the sum of m and o is 3 wherein one CH$_2$ may be replaced with S or O and 1 —CH$_2$—CH$_2$ may be replaced by —CH=CH— or —C≡C—.

In another embodiment, the sum of m and o is 2 wherein one CH$_2$ may be replaced with S or O or 1 —CH$_2$—CH$_2$ may be replaced by —CH=CH— or —C≡C—.

In another embodiment, the sum of m and o is 4 wherein one CH$_2$ may be replaced with S or O and 1 —CH$_2$—CH$_2$ may be replaced by —CH=CH— or —C≡C—.

Interarylene or heterointerarylene refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has substituents in addition to the two parts of the molecule it connects.

In one embodiment, Ar is substituted or unsubstituted interphenylene, interthienylene, interfurylene, interpyridinylene, interoxazolylene, and interthiazolylene. In another embodiment Ar is interphenylene (Ph). In another embodiment A is —(CH$_2$)$_2$—Ph—. While not intending to limit scope of the invention in any way, substituents may have 4 or less heavy atoms, wherein the heavy atoms are C, N, O, S, P, F, Cl, Br, and/or I in any stable combination. Any number of hydrogen atoms required for a particular substituent will also be included. In addition to the atoms listed above, a substituent may also have a metal cation or any other stable cation having an atom not listed above if the substituent is acidic and the salt form is stable. For example, —OH may form an —O$^-$Na$^+$ salt or CO$_2$H may form a CO$_2^-$K$^+$ salt. Any cation of the salt is not counted in the "4 or less heavy atoms."

Thus, the substituent may be hydrocarbyl, i.e. a moiety consisting of only carbon and hydrogen, including linear, branched or cyclic hydrocarbyl, and combinations thereof; having up to 4 carbon atoms, including alkyl up to C$_4$, alkenyl, alkynyl, and the like;

hydrocarbyloxy, i.e. —O-hydrocarbyl, up to C$_3$;

organic acid such as CO$_2$H, SO$_3$H, P(O)(OH)$_2$, and the like, and salts thereof;

CF$_3$;

halo, such as F, Cl, or Br;

hydroxyl;

NH$_2$ and alkylamine functional groups up to C$_3$;

other N or S containing substituents such as CN, NO$_2$, and the like;

and the like.

In one embodiment A is —(CH$_2$)$_m$—Ph—(CH$_2$)$_o$— wherein the sum of m and o is 1, 2, or 3, and wherein one CH$_2$ may be replaced with S or O.

In another embodiment A is —CH$_2$—Ar—OCH$_2$—. In another embodiment A is —CH$_2$—Ph—OCH$_2$—. In another embodiment, Ph is attached at the 1 and 3 positions, otherwise known as m-interphenylene, such as when A has the structure shown below.

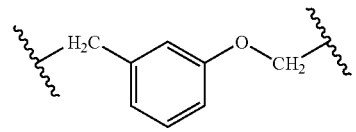

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced with S or O; or A is —(CH$_2$)$_2$-Ph— wherein one CH$_2$ may be replaced with S or O.

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced with S or O; or A is —(CH$_2$)$_2$—Ph—.

In one embodiment, Ar is thienyl.

In other embodiments, A has one of the following structures.

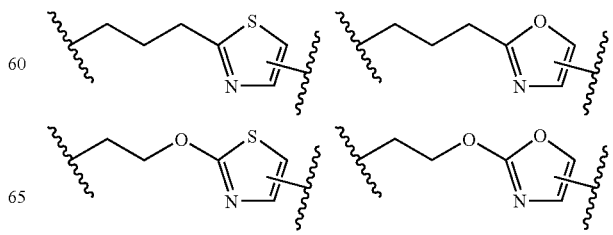

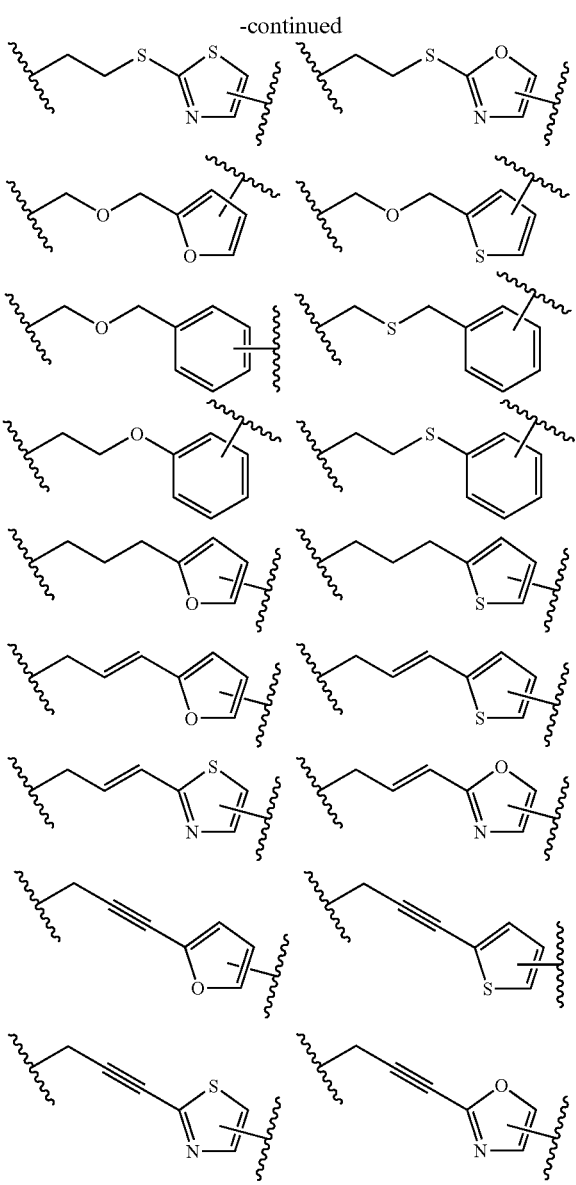

In another embodiment A is —CH₂OCH₂Ar.
In another embodiment A is —CH₂SCH₂Ar.
In another embodiment A is —(CH₂)₃Ar.
In another embodiment A is —CH₂O(CH₂)₄.
In another embodiment A is —CH₂S(CH₂)₄.
In another embodiment A is —(CH₂)₆—.
In another embodiment A is cis —CH₂CH=CH—(CH₂)₃—.
In another embodiment A is —CH₂C≡C—(CH₂)₃—.
In another embodiment A is —S(CH₂)₃S(CH₂)₂—.
In another embodiment A is —(CH₂)₄OCH₂—.
In another embodiment A is cis —CH₂CH=CH—CH₂OCH₂—.
In another embodiment A is —CH₂CH≡CH—CH₂OCH₂—.
In another embodiment A is —(CH₂)₂S(CH₂)₃—.
In another embodiment A is —CH₂—Ph—OCH₂—, wherein Ph is interphenylene.
In another embodiment A is —CH₂-mPh—OCH₂—, wherein mPh is m-interphenylene.

In another embodiment A is —CH₂—O—(CH₂)₄—.
In another embodiment A is —CH₂—O—CH₂—Ar—, wherein Ar is 2,5-interthienylene.
In another embodiment A is —CH₂—O—CH₂—Ar—, wherein Ar is 2,5-interfurylene.
In another embodiment A is (3-methylphenoxy)methyl.
In another embodiment A is (4-but-2-ynyloxy)methyl.
In another embodiment A is 2-(2-ethylthio)thiazol-4-yl.
In another embodiment A is 2-(3-propyl)thiazol-5-yl.
In another embodiment A is 3-(methoxymethyl)phenyl.
In another embodiment A is 3-(3-propylphenyl).
In another embodiment A is 3-methylphenethyl.
In another embodiment A is 4-(2-ethyl)phenyl.
In another embodiment A is 4-phenethyl.
In another embodiment A is 4-methoxybutyl.
In another embodiment A is 5-(methoxymethyl)furan-2-yl.
In another embodiment A is 5-(methoxymethyl)thiophen-2-yl.
In another embodiment A is 5-(3-propyl)furan-2-yl.
In another embodiment A is 5-(3-propyl)thiophen-2-yl.
In another embodiment A is 6-hexyl.
In another embodiment A is (Z)-6-hex-4-enyl.

U¹ is H, O; OH, I, Br, Cl, F, CF₃, CN, or CH₂OH. Thus, the structures below are possible. Each structure below represents a specific embodiment which is individually contemplated, as well as pharmaceutically acceptable salts and prodrugs of compounds which are represented by the structures.

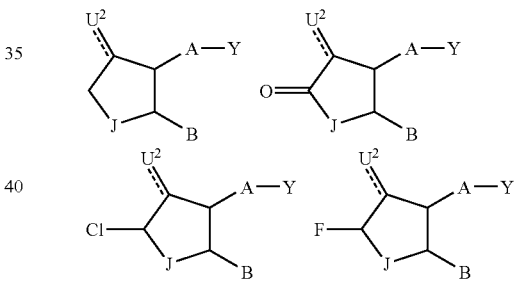

U² is H, O; OH, I, Br, Cl, F, CF₃, CN, or CH₂OH. Thus, the structures below are possible. Each structure below represents a specific embodiment which is individually contemplated, as well as pharmaceutically acceptable salts and prodrugs of compounds which are represented by the structures.

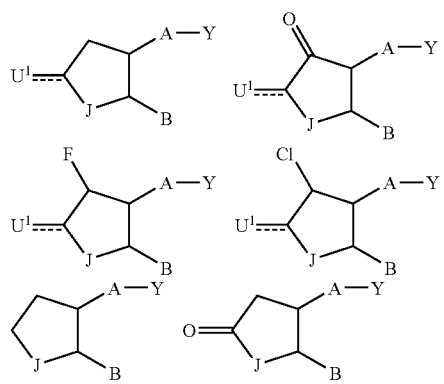

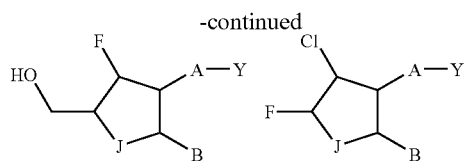

J is

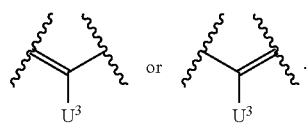

Thus, the structures below are possible. Each structure below represents a specific embodiment which is individually contemplated, as well as pharmaceutically acceptable salts and prodrugs of compounds which are represented by the structures.

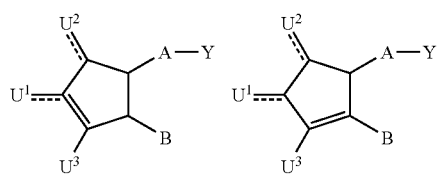

$U^3$ is H, OH, I, Br, Cl, F, CN, $C_{1-6}$ alkyl, aryl, or heteroaryl, or $C_{1-6}$ hydroxyalkyl. Thus, the structures below are possible. Each structure below represents a specific embodiment which is individually contemplated, as well as pharmaceutically acceptable salts and prodrugs of compounds which are represented by the structures.

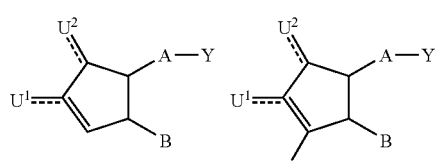
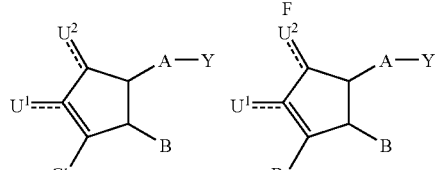
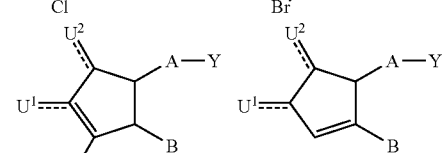
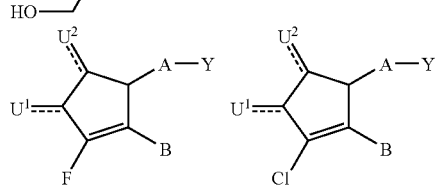

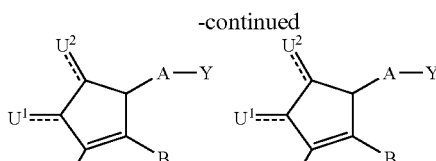
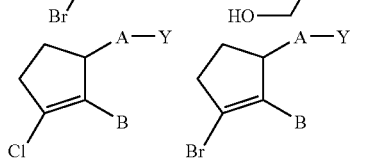
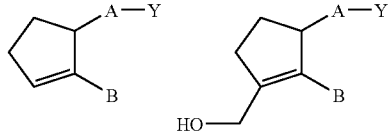
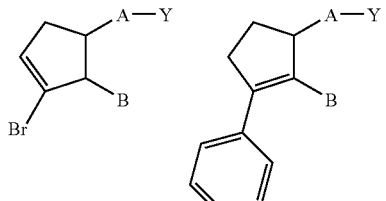
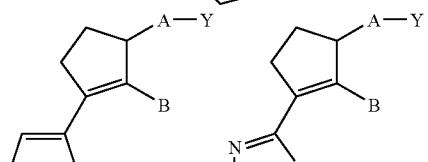
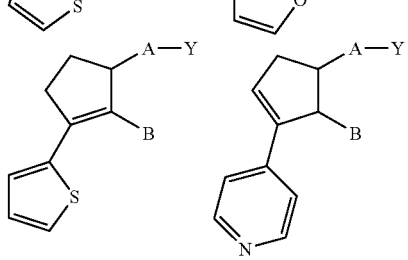

Aryl and heteroaryl with regard to $U^3$ is the same as that of B.

Compounds according to either of the two tautomeric forms shown below are also contemplated. For any structure depicted herein, any tautomer or tautomeric forms of the compound depicted by the structure are considered to be included in compounds of that structure.

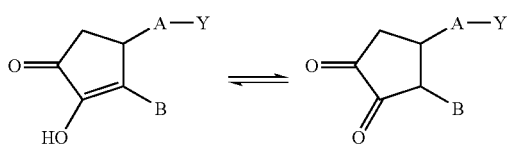

Thus, if the structure on the left is depicted herein, it is intended to cover the tautomer depicted on the right and any other tautomers or tautomeric forms that may exist.

B is aryl or heteroaryl.

Aryl is an aromatic ring or ring system such as phenyl, naphthyl, biphenyl, and the like.

Heteroaryl is aryl having one or more N, O, or S atoms in the ring, i.e. one or more ring carbons are substituted by N, O, and/or S. While not intending to be limiting, examples of heteroaryl include thienyl, pyridinyl, furyl, benzothienyl, benzofuryl, imidizololyl, indolyl, and the like.

A substituent of aryl or heteroaryl should be stable and may have up to 20 non-hydrogen atoms each and as many hydrogen atoms as necessary, wherein the non-hydrogen atoms are C, N, O, S, P, F, Cl, Br, and/or I in any stable combination. However, the total number of non-hydrogen atoms on all of the substituents combined must also be 20 or less. In addition to the atoms listed above, a substituent may also have a metal cation or other stable cation having an atom not listed above if the substituent is acidic and the salt form is stable. For example, —OH may form an —O$^-$Na$^+$ salt or CO$_2$H may form a CO$_2^-$K$^+$ salt. Any cation of the salt is not counted in the 20 non-hydrogen atoms.

Thus, while not intending to limit the scope of the invention in any way, a substituent may be:

hydrocarbyl, i.e. a moiety consisting of only carbon and hydrogen such as alkyl, alkenyl, alkynyl, and the like, including linear, branched or cyclic hydrocarbyl, and combinations thereof;

hydrocarbyloxy, meaning O-hydrocarbyl such as OCH$_3$, OCH$_2$CH$_3$, O-cyclohexyl, etc, up to 19 carbon atoms;

other ether substituents such as CH$_2$OCH$_3$, (CH$_2$)$_2$OCH(CH$_3$)$_2$, and the like;

thioether substituents including S-hydrocarbyl and other thioether substituents;

hydroxyhydrocarbyl, meaning hydrocarbyl-OH, including hydroxyalkyl, such as CH$_2$OH, C(CH$_3$)$_2$OH, etc, up to 19 carbon atoms;

nitrogen substituents such as NO$_2$, CN, and the like, including amino, such as NH$_2$, NH(CH$_2$CH$_3$OH), NHCH$_3$, and the like;

carbonyl substituents, such as CO$_2$H, ester, amide, and the like;

halogen, such as chloro, fluoro, bromo, and the like fluorocarbyl, such as CF$_3$, CF$_2$CF$_3$, etc.;

phosphorous substituents, such as PO$_3^{2-}$, and the like;

sulfur substituents, including S-hydrocarbyl, SH, SO$_3$H, SO$_2$-hydrocarbyl, SO$_3$-hydrocarbyl, and the like.

Substituted aryl or heteroaryl may have as many substituents as the ring or ring system will bear, and the substituents may be the same or different. Thus, for example, an aryl ring or a heteroaryl ring may be substituted with chloro and methyl; methyl, OH, and F; CN, NO$_2$, and ethyl; and the like including any conceivable substituent or combination of substituent possible in light of this disclosure.

Substituted aryl or substituted heteroaryl also includes a bicyclic or polycyclic ring system wherein one or more rings are aromatic and one or more rings are not. For example, indanonyl, indanyl, indanolyl, tetralonyl, and the like are substituted aryl and are also substituted phenyl. For this type of polycyclic ring system, an aromatic or heteroaromatic ring, not a non-aromatic ring, must be attached to the remainder of the molecule, i.e. the part of the molecule that is not B. In other words, in any structure depicting —B herein, where — is a bond, the bond is a direct bond to an aromatic ring.

Hydrocarbyl is a moiety consisting of carbon and hydrogen, including, but not limited to:

1. alkyl, which is hydrocarbyl containing no double or triple carbon-carbon bonds; alkyl includes, but is not limited to:
    linear alkyl, cyclic alkyl, branched alkyl, and combinations thereof;
    C$_{1-3}$ alkyl, which refers to alkyl having 1, 2, or 3 carbon atoms, including, but no limited to, methyl, ethyl, isopropyl, cyclopropyl, n-propyl, and the like;
    C$_{1-6}$ alkyl, which refers to alkyl having 1, 2, 3, 4, 5, or 6 carbon atoms; including, but not limited to methyl, ethyl, propyl isomers, cyclopropyl, butyl isomers, cyclobutyl, pentyl isomers, cyclopentyl, hexyl isomers, cyclohexyl, and the like;
    combinations of these terms are possible, and their meanings should be obvious to those of ordinary skill in the art; for example C$_{1-6}$ linear alkyl would refer to C$_{1-6}$ alkyl which is also linear;
2. alkenyl, which is hydrocarbyl containing one or more carbon-carbon double bonds; alkenyl includes, but is not limited to:
    linear alkenyl, cyclic alkenyl, branched alkenyl, and combinations thereof;
    alkenyl having 1, 2, 3, or more carbon-carbon double bonds;
3. alkynyl, which is hydrocarbyl containing one or more carbon-carbon triple bonds; alkynyl includes, but is not limited to:
    linear alkynyl, cyclic alkynyl, branched alkynyl, and combinations thereof;
    alkynyl having 1, 2, 3, or more carbon-carbon double bonds;
4. aryl, provided that it contains no heteroatoms either in a ring or as a substituent; and
5. combinations of any of the above;
    C$_{1-6}$ hydroxylalkyl is hydroxyalkyl having 1, 2, 3, 4, 5, or 6 carbon atoms.

In another embodiment, B is substituted or unsubstituted phenyl.

In another embodiment, B is substituted or unsubstituted thienyl.

In another embodiment, B is substituted or unsubstituted naphthyl.

In another embodiment, B is substituted or unsubstituted furyl.

In another embodiment, B is substituted or unsubstituted pyridinyl.

In another embodiment, B is substituted or unsubstituted benzothienyl.

In another embodiment, B is substituted or unsubstituted indanyl.

In another embodiment, B is substituted or unsubstituted tetralonyl.

In another embodiment, B has 1, 2, 3, 4, or 5 substituents, wherein each substituent has one or more carbon, fluorine, chlorine, bromine, oxygen, sulfur, or atoms; and wherein all substituents taken together consist of 0, 1, 2, 3, 4, 5, 6, 7, 8, 9 or 10 carbon atoms; 0, 1, 2, 3, 4, 5, 6, 7, 8 or 9 fluorine atoms; 0, 1, 2 or 3 chlorine atoms, 0, 1, 2 or 3 bromine atoms, 0, 1, 2 or 3 oxygen atoms; 0, 1, 2, or 3 sulfur atoms; 0, 1, 2, or 3 nitrogen atoms; and from 0 to 24 hydrogen atoms.

In another embodiment, B has 1, 2, 3, 4, or 5 substituents, wherein each substituent has one or more carbon, fluorine, chlorine, bromine, or oxygen atoms; and wherein all substituents taken together consist of 0, 1, 2, 3, 4, 5, 6, 7, 8, 9 or 10 carbon atoms; 0, 1, 2, 3, 4, 5, 6, 7, 8 or 9 fluorine atoms; 0, 1, 2 or 3 chlorine atoms, 0, 1, 2 or 3 bromine atoms; 0, 1, 2 or 3 oxygen atoms; and from 0 to 24 hydrogen atoms.

In another embodiment, B has a substituent of the formula C$_a$H$_b$O$_c$; wherein a is 0, 1, 2, 3, 4, 5, 6, 7, 8 or 9, b is 0, 1, 2, 3, 4, 5, 6, 7, 8, 9, 10, 11, 12, 13, 14, 15, 16, 17, 18 or 19; and c is 0, 1, 2, or 3.

In another embodiment, B has 1, 2, 3, or 4 alkyl substituents having 1, 2, 3, 4, 5, 6, 7, 8, 9 or 10 carbon atoms.

In another embodiment, B has a hydroxyalkyl substituent; said hydroxyalkyl substituent having 0, 1, 2, 3, 4, 5, 6, 7, 8, 9 or 10 carbon atoms and 1 or 2 hydroxy moieties.

In another embodiment, B has an alkyl substituent having 0, 1, 2, 3, 4, 5, 6, 7, 8, 9 or 10 carbon atoms.

Examples of useful moieties for B are depicted below. Each is individually contemplated as an embodiment.

Structure: 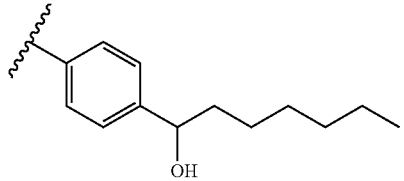

Name: 4-(1-hydroxyheptyl)phenyl

Structure: 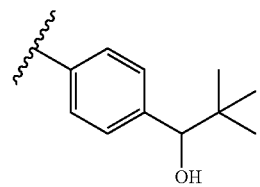

Name: 4-(1-hydroxy-2,2-dimethylpropyl)phenyl

Structure: 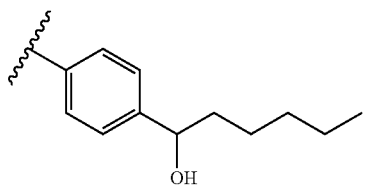

Name: 4-(1-hydroxyhexyl)phenyl

Structure: 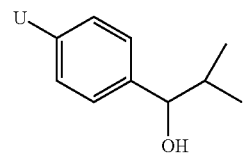

Name: 4-(1-hydroxy-2-methylpropyl)phenyl

Structure: 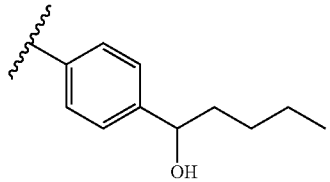

Name: 4-(1-hydroxypentyl)phenyl

Structure: 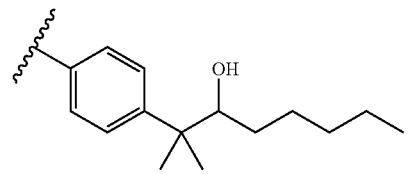

Name: 4-(3-hydroxy-2-methyloctan-2-yl)phenyl

Structure: 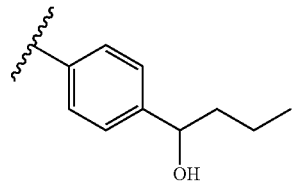

Name: 4-(1-hydroxybutyl)phenyl

Structure: 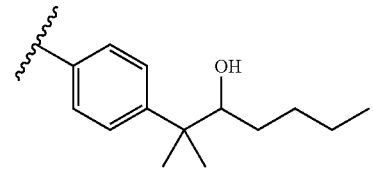

Name: 4-(3-hydroxy-2-methylheptan-2-yl)phenyl

Structure: 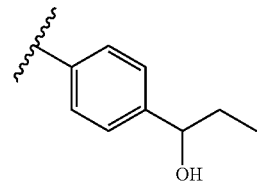

Name: 4-(1-hydroxypropyl)phenyl

Structure: 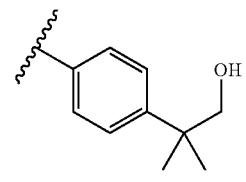

Name: 4-(1-hydroxy-2-methylpropan-2-yl)phenyl

Structure: 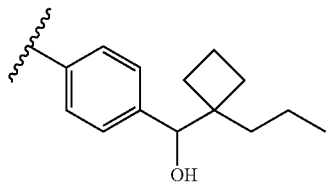

Name: 4-(hydroxy(1-propylcyclobutyl)methyl)phenyl

Structure: 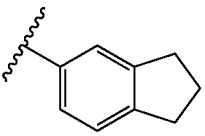

Name: 2,3-dihydro-1H-inden-5-yl

-continued

| Structure: | 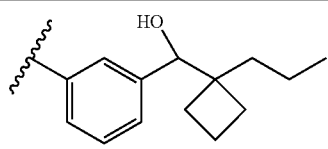 | 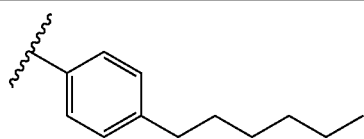 |
|---|---|---|
| Name: | 3-(hydroxy(1-propylcyclobutyl)methyl)phenyl | 4-hexylphenyl |
| Structure: | 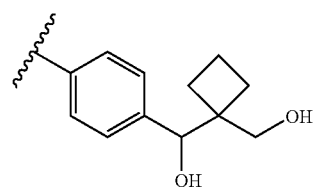 | 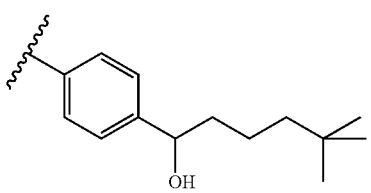 |
| Name: | 4-(hydroxy(1-(hydroxymethyl)cyclobutyl)methyl)phenyl | 4-(1-hydroxy-5,5-dimethylhexyl)phenyl |
| Structure: | 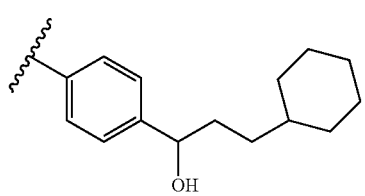 | 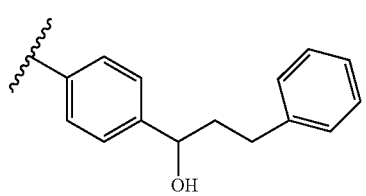 |
| Name: | 4-(3-cyclohexyl-1-hydroxypropyl)phenyl | 4-(1-hydroxy-3-phenylpropyl)phenyl |
| Structure: | 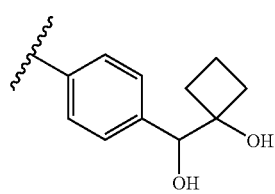 | 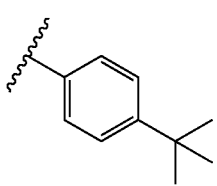 |
| Name: | 4-(hydroxy(1-hydroxycyclobutyl)methyl)phenyl | 4-tert-butylphenyl |
| Structure: | 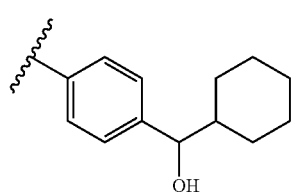 | 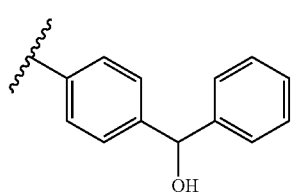 |
| Name: | 4-(cyclohexyl(hydroxy)methyl)phenyl | 4-(hydroxy(phenyl)methyl)phenyl |
| Structure: | 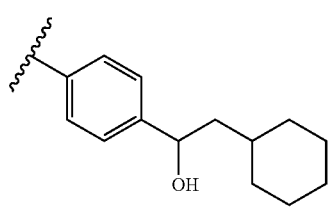 | 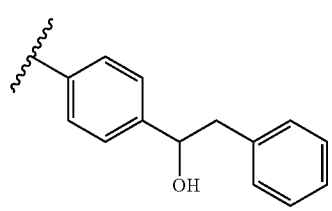 |
| Name: | 4-(2-cyclohexyl-1-hydroxyethyl)phenyl | 4-(1-hydroxy-2-phenylethyl)phenyl |
| Structure: | 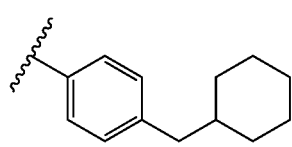 | 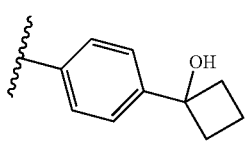 |
| Name: | 4-(cyclohexylmethyl)phenyl | 4-(1-hydroxycyclobutyl)phenyl |

-continued

| Structure: | 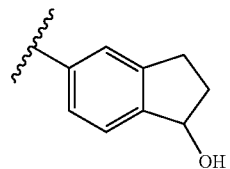 | 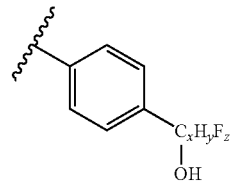 |
|---|---|---|
| Name: | 1-hydroxy-2,3-dihydro-1H-inden-5-yl | |
| Structure: | 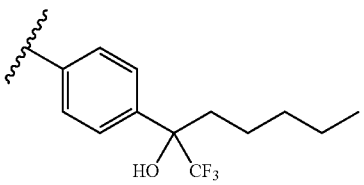 | 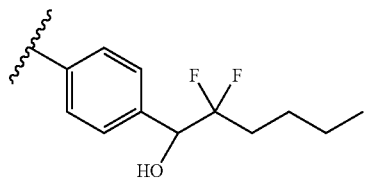 |
| Name: | 4-(1,1,1-trifluoro-2-hydroxyheptan-2-yl)phenyl | 4-(2,2-difluoro-1-hydroxyhexyl)phenyl |

In the above embodiments, x is 5, 6, or 7, and y+z is 2x+1.

In one embodiment, x is 5 and y+z is 11.

In another embodiment, x is 6 and y+z is 13.

In another embodiment, x is 7 and y+z is 15.

A compound, substituent, moiety, or any structural feature is stable if it is sufficiently stable for the compound to be isolated for at least 12 hours at room temperature under normal atmospheric conditions, or if it is sufficiently stable to be useful for at least one use disclosed herein.

The term aromatic refers to the meaning commonly understood in the art, i.e. it refers to an unsaturated, fully conjugated ring having 4N+2 ring electrons (e.g. 2, 6, 10, etc.) Thus, phenyl, pyridinyl, thienyl, furyl, and the like are aromatic. Aryl is a moiety that is aromatic.

A heavy atom is an atom which is not hydrogen.

A heteroatom is an atom which is not carbon or hydrogen.

A pharmaceutically acceptable salt is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt. Examples of useful salts include, but are not limited to, sodium salts, potassium salts, calcium salts, ammonium salts and the like.

Unless otherwise indicated, reference to a compound should be construed broadly to include pharmaceutically acceptable salts, tautomers, and prodrugs of the depicted structure.

Unless stereochemistry is explicitly depicted, a structure is intended to include every possible stereoisomer, both pure or in any possible mixture. In particular, compounds having the stereochemistry indicated in the structures below are contemplated.

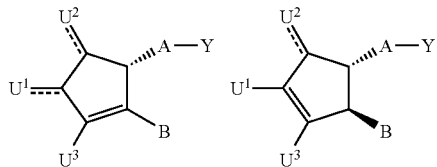

A person of ordinary skill in the art understands the meaning of the stereochemistry associated with the hatched wedge/solid wedge structural features. For example, an introductory organic chemistry textbook (Francis A. Carey, Organic Chemistry, New York: McGraw-Hill Book Company 1987, p. 63) states "a wedge indicates a bond coming from the plane of the paper toward the viewer" and the hatched wedge "represents a bond receding from the viewer." Unless stereochemistry is explicitly depicted, a structure is intended to include every possible stereoisomer, both pure or in any possible mixture.

For the purposes of this disclosure, "treat," "treating," or "treatment" refer to the use of a compound, composition, therapeutically active agent, or drug in the diagnosis, cure, mitigation, treatment, prevention of disease or other undesirable condition, or to affect the structure or any function of the body of man or other animals.

The compounds disclosed herein are useful in the manufacture of a medicament for the treatment of glaucoma or ocular hypertension in a mammal.

Another embodiment is a medicament comprising a compound disclosed herein, wherein said composition is a liquid which is ophthalmically acceptable.

Another embodiment is a method comprising administering a compound disclosed herein to a mammal for the treatment of glaucoma or ocular hypertension.

Another embodiment is a kit comprising a composition comprising compound disclosed herein, a container, and instructions for administration of said composition to a mammal for the treatment of glaucoma or ocular hypertension.

Applications for Stimulating Hair Growth

In one embodiment, the compounds disclosed herein can be useful in the treatment of baldness and/or hair loss. Alopecia (baldness) is a deficiency of either normal or abnormal hair, and is primarily a cosmetic problem in humans. It is a deficiency of terminal hair, the broad diameter, colored hair that is readily seen. However, in the so called bald person, although there is a noticeable absence of terminal hair, the skin does contain vellus hair, which is a fine colorless hair which may require microscopic examination to determine its presence. This vellus hair is a precursor to terminal hair.

The compounds described herein can be used to stimulate, such as the conversion of vellus hair to growth as terminal hair, as well as increasing the rate of growth of terminal hair. The utility of the compounds described herein for the simulation of hair growth was discovered as follows.

In the course of treating patients having glaucoma, treatment may only be appropriate in one eye. Within the course of daily practice, it was discovered that a patient who had been treated with bimatoprost, a prostaglandin analogue, developed lashed that were longer, thicker, and fuller in the treated eye than in the non-treated eye. On examination, the difference was found to be very striking. The lashes were longer and had a fuller, denser appearance in the treated eye. The lash appearance on the lids of the treated eyes would have appeared quite attractive if it represented a bilateral phenomenon. As a result of its asymmetric nature, the long lashes on one side could be construed as disturbing from a cosmetic standpoint. A systemic examination was preformed as a result of the asymmetric phenomenon. It soon became apparent that this altered appearance was not an isolated finding. Comparison of the lids of patients who were taking bimatoprost in only one eye revealed subtle changes in the lashed and adjacent hairs of the bimatoprost-treated side in several patients. Definite differences could be identified to varying degrees in the lashes and adjacent hairs of all patients who were taking the drug on a unilateral basis for longer than 6 months.

The changes in the lashes were apparent on gross inspection in several patients once attention was focused on the issue. In those with light colored hair and lashes, the differences were only seen easily with the aid of the high magnification and lighting capabilities of the slit lamp biomicroscope. In the course of glaucoma follow-up examination, attention is generally immediately focused on the eye itself. As a result of the high power magnification needed only one eye is seen at a time and the eye is seen at a high enough power that the lashes are not in focus. At these higher powers, any lash asymmetry between the two eyes is not likely to be noticed except by careful systematic comparison of the lashes and adjacent hairs of the eyelids of the two eyes.

Observed parameters leading to the conclusion that more robust hair growth occurred in the treatment area following administration of the prostaglandin analogue were multiple. They included increased length of lashed, increased number of lashes along the normal lash line, increased thickness and luster of lashes, increased auxiliary lash-like terminal hair in transitional areas adjacent to areas of normal lash growth, increased auxiliary lash-like terminal hairs at the medial and lateral canthal area, increased pigmentation of the lashes, increased numbers, increased length, as well as increased luster, and thickness of fine hair on the skin of the adjacent lid, and finally, increased perpendicular angulation of lashes and lash-like terminal hairs. The conclusion that hair growth is stimulated by prostaglandin analogues such as bimatoprost is thus supported not by evidence of a difference in a single parameter, but is based on multiple parameters of hair appearance in treated versus control areas in many subjects.

The compounds described herein are prostaglandin analogues and therefore have similar activities as bimatoprost, contain structural similarities, and therefore are expected to stimulate hair growth and stimulation of the conversion of vellus hair to terminal hair. In one embodiment, the compounds described herein and their prodrugs can be used for the stimulation of hair growth. As used herein, hair growth includes hair associated with the scalp, eyebrows, eyelids, beard, and other areas of the skin of animals.

In one embodiment, the compound is mixed with a dermatologically compatible vehicle or carrier. The vehicle, which may be employed for preparing compositions as described herein, may comprise, for example, aqueous solutions such as e.g., physiological salines, oil solutions, or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

In one embodiment, dermatological compositions can be formulated for topical treatment for the stimulation of hair growth which comprises an effective hair growth simulating amount of one or more compounds as defined above and a dermatologically compatible carrier. Effective amounts of the active compounds may be determined by one of ordinary skill in the art, but will vary depending on the compound employed, frequency of application and desired result. The compound will generally range from about 0.0000001 to about 50% by weight of the dermatological composition. Preferably, the compound will range from about 0.001 to about 50% by weight of total dermatological composition, more preferably from about 0.1 to about 30% by weight of the composition.

In one embodiment, the application of the present compounds for stimulation of hair growth finds applications in mammalian species, including both humans and animals. In humans, the compounds described herein can be applied for example, to the scalp, face beard, head, pubic area, upper lip, eyebrows, and eyelids. In animal raised for their pelts, e.g., mink, the compounds described herein can be applied over the entire surface of the body to improve the overall pelt for commercial reasons. The process can also be used for cosmetic reasons in animals, e.g., applied to the skin of dogs and cats having bald patches due to mange or other diseases causing a degree of alopecia.

The pharmaceutical compositions contemplated for the stimulation of hair growth include pharmaceutical compositions suited for topical and local action. The term "topical" as employed herein relates to the use of a compound, as described herein, incorporated in a suitable pharmaceutical carrier, and applied at the site of thinning hair or baldness for exertion of local action. Accordingly, such topical compositions include those pharmaceutical forms in which the compound is applied externally by direct contact with the skin to be treated. Conventional pharmaceutical forms for this purpose include ointments, liniments, creams, shampoos, lotions, pastes, jellies, sprays, aerosols, and the like, and may be applied in patches or impregnated dressings depending on the part of the body to be treated. The term "ointment" embraces formulations (including creams) having oleaginous, water-soluble and emulsion-type bases, e.g., petrolatum, lanolin, polyethylene glycols, as well as mixtures of these.

Typically, the compounds can be applied repeatedly for the sustained period of time topically on the part of the body to be treated, for example, the eyelids, eyebrows, skin or scalp. The preferred dosage regimen will generally involve regular, such as daily, administration for a period of treatment of at least one month, more preferably at least three months, and most preferably, at least six months.

For topical use on the eyelids or eyebrows, the active compounds can be formulated in aqueous solutions, creams, ointments, or oils exhibiting physiological acceptable osmolarity by addition of pharmaceutically acceptable buffers and salts. such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid and the like as additives. Furthermore, particularly aqueous solutions may contain viscosity increasing agents such as polysaccharides, e.g., methylcellulose, mucopolysaccharides, e.g., hyaluronic acid and chondroitin sulfate, or poly alcohol, e.g., polyvinylalcohol. Various slow releasing gels and matricies may also be employed as well as soluble and insoluble ocular inserts, for instance, based on substances forming in situ gels. Depending on the actual formation and compound to be used, various amounts of the drug and different dose regimens may be employed. Typically, the daily amount of compound for treatment of the eyelid may be about 0.1 ng to about 100 mg per eyelid.

For topical use on the skin and scalp, the compound can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betain, chlorhexidine, benzalkonium chloride, and the like. Various matricies for the slow release delivery may also be used. Typically, the dose to be applied on the scalp is in the range of about 0.1 ng to about 100 mg per day, more preferably about 1 ng to about 10 mg per day, and most preferably about 10 ng to about 1 mg per day depending on the compound and the formulation. To achieve the daily amount of medication depending on the formulation, the compound may be administered once or several times daily with or without anti oxidants.

Synthetic Methods

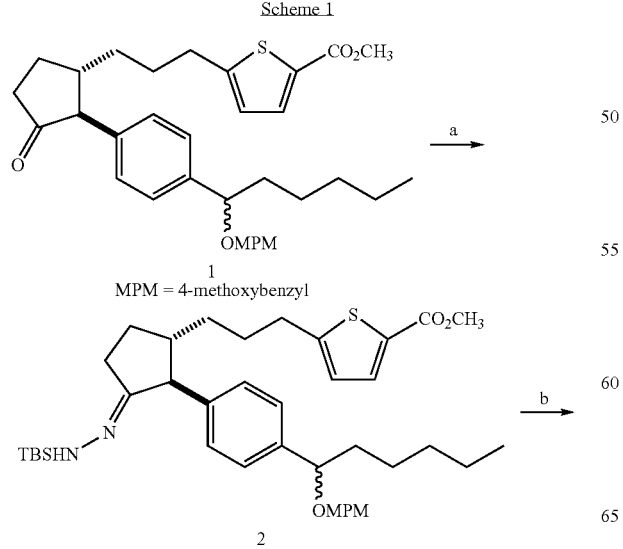

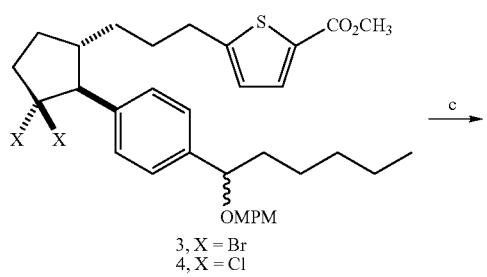

3, X = Br
4, X = Cl

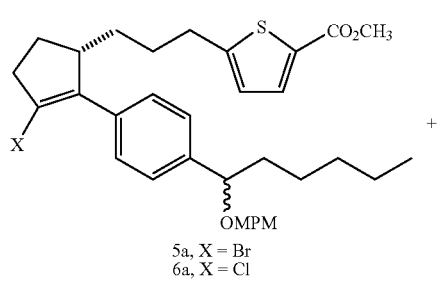

5a, X = Br
6a, X = Cl

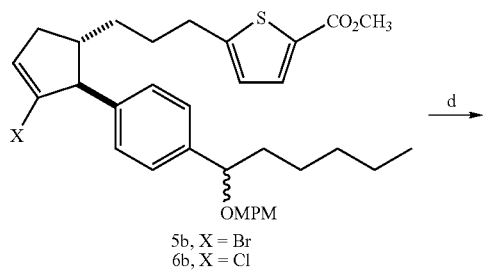

5b, X = Br
6b, X = Cl

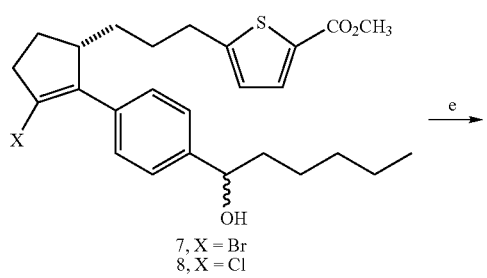

7, X = Br
8, X = Cl

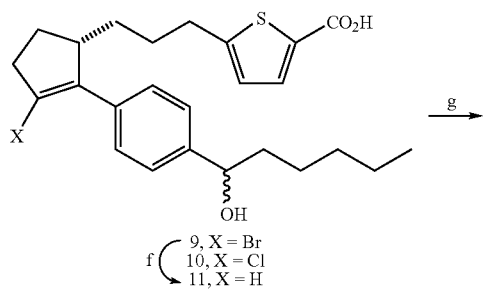

9, X = Br
10, X = Cl
11, X = H

-continued

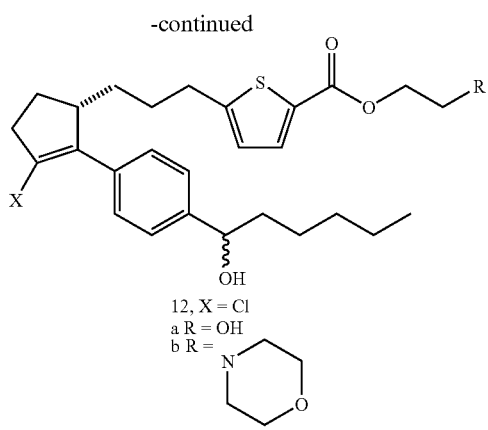

12, X = Cl
a R = OH
b R = ![morpholine-ethyl group]

Conditions: (a) (TBSNH)₂, cat. Sc(OTf)₃, CHCl₃; (b) CuCl₂, Et₃N, MeOH; (c) 2-t-Butyl-1,1,3,3-tetramethylguanidine, ClCH₂CH₂Cl, rt or 60° C.; (d) DDQ, CH₂Cl₂/H₂O; (e) 1 M LiOH, THF 60° C.; (f) tert-BuLi; MeOH; (g) 1. ClCO₂Et, Et₃N, CH₂Cl₂ 2. RCH₂CH₂OH.

TBS hydrazone of 5-[3-((1S,2S)-2-{4-[1-(4-Methoxy-benzyloxy)-hexyl]-phenyl}-3-oxo-cyclopentyl)-propyl]-thiophene-2-carboxylic acid methyl ester (2). The procedure of Furrows, M. E.; Myers, A. G. *J. Am. Chem. Soc.* 2004, 126, 5436 was followed: A solution of Sc(OTf)₃ (170 µL, 0.0017 mmol, 0.01 M/CH₃CN) was evaporated. A solution of ketone 1 (U.S. Provisional Patent Application No. 60/746,386 filed on May 4, 2006, 93 mg, 0.165 mmol) in 1 mL CHCl₃ was added by cannula, rinsing with 1 mL CHCl₃. The reaction was cooled in an ice bath and a solution of (TBSNH)₂ in 0.5 mL CHCl₃ was added, rinsing with 0.5 mL CHCl₃. After 30 min. at 0° C., the reaction was allowed to warm to room temperature (rt) overnight. The volatiles were evaporated under N₂ stream then at 1 mbar (30 min. at room temperature and 30 min. at 35° C.). The crude hydrazone was used directly in subsequent reactions.

5-[3-((1S,2S)-3,3-Dibromo-2-{4-[1-(4-methoxy-benzyloxy)-hexyl]-phenyl}-cyclopentyl)-propyl]-thiophene-2-carboxylic acid methyl ester (3). A solution of Hydrazone 2 (prepared from 0.21 mmol of ketone as described above) in 1 mL CHCl₃ was cannula transferred to a mixture of CuBr₂ (325 mg, 1.46 mmol) and Et₃N (90 µL, 0.65 mmol) in MeOH (2.2 mL), rinsing with 1 mL CHCl₃. After 1 h, a solution of 10% conc. NH₄OH/saturated NH₄Cl was added and the mixture was extracted with CH₂Cl₂ (3×25 mL). The combined CH₂Cl₂ solution was dried (Na₂SO₄), filtered and evaporated. Purification by flash chromatography (20% ethyl acetate/hexanes) gave compound 3 (52 mg, 35%).

5-[3-((1S,2S)-3,3-Dichloro-2-{4-[1-(4-methoxy-benzyloxy)-hexyl]-phenyl}-cyclopentyl)-propyl]-thiophene-2-carboxylic acid methyl ester (4). A solution of Hydrazone 2 (prepared from 0.11 mmol of ketone as described above) in 1 mL CHCl₃ was cannula transferred to a mixture of CuCl₂ (107 mg, 0.80 mmol) and Et₃N (50 µL, 0.36 mmol) in MeOH (1.2 mL), rinsing with 1 mL CHCl₃. After 1 h, a solution of 10% conc. NH₄OH/saturated NH₄Cl (8 mL) was added and the mixture was extracted with CH₂Cl₂ (3×30 mL). The combined CH₂Cl₂ solution was dried (Na₂SO₄), filtered and evaporated. Purification by flash chromatography (0%→20% ethyl acetate/hexanes) gave compound 4 (34 mg, 49%).

5-[3-((S)-3-Bromo-2-{4-[1-(4-methoxy-benzyloxy)-hexyl]-phenyl}-cyclopent-2-enyl)-propyl]-thiophene-2-carboxylic acid methyl ester (5a). A solution of dibromide 3 (52 mg, 0.074 mmol) and 2-tert-butyl-1,1,3,3-tetramethylguanidine (BTMG, 0.8 mL) in 1,2-dichloroethane (2 mL) was stirred at room temperature. After 3 days, 1 M HCl was added and the mixture was extracted with CH₂Cl₂ (3×25 mL). The combined dichloromethane solution was dried (Na₂SO₄), filtered and evaporated. Purification by flash chromatography (0%→20% ethyl acetate/hexanes) gave compound 5a contaminated with 15% of the alkene regioisomer 5b as an inseparable mixture (45 mg, 97%).

5-[3-((S)-3-Chloro-2-{4-[1-(4-methoxy-benzyloxy)-hexyl]-phenyl}-cyclopent-2-enyl)-propyl]-thiophene-2-carboxylic acid methyl ester (6a). A solution of dichloride 4 (12 mg, 0.019 mmol) and 2-tert-butyl-1,1,3,3-tetramethylguanidine (BTMG, 0.2 mL) in 1,2-dichloroethane (0.5 mL) was stirred at 60° C. After 70 h, 1 M HCl (28 mL) was added and the mixture was extracted with 20 mL CH₂Cl₂. The dichloromethane solution was washed further with 1 M HCl (3×25 mL) and then was dried (Na₂SO₄), filtered and evaporated. Purification by flash chromatography (0%→15% ethyl acetate/hexanes) gave compound 6a, contaminated with 15% of the alkene regioisomer 6b as an inseparable mixture (10 mg, 93%).

5-(3-{(S)-3-Bromo-2-[4-(1-hydroxy-hexyl)-phenyl]-cyclopent-2-enyl}-propyl)-thiophene-2-carboxylic acid methyl ester (7) and 5-(3-{(S)-3-Chloro-2-[4-(1-hydroxy-hexyl)-phenyl]-cyclopent-2-enyl}-propyl)-thiophene-2-carboxylic acid methyl ester (8). The previously described DDQ procedure was used (U.S. Pat. No. 7,091,231), which gave compounds 7 and 8, contaminated with 15% of the alkene regioisomer as inseparable mixtures.

5-(3-{(S)-3-Bromo-2-[4-(1-hydroxy-hexyl)-phenyl]-cyclopent-2-enyl}-propyl)-thiophene-2-carboxylic acid (9) and 5-(3-{(S)-3-Chloro-2-[4-(1-hydroxy-hexyl)-phenyl]-cyclopent-2-enyl}-propyl)-thiophene-2-carboxylic acid (10). The previously described LiOH procedure was used at 60° C. overnight (U.S. Pat. No. 7,091,231), which gave compounds 9 and 10, contaminated with 15% of the alkene regioisomer as inseparable mixtures.

5-(3-{(S)-2-[4-(1-Hydroxy-hexyl)-phenyl]-cyclopent-2-enyl}-propyl)-thiophene-2-carboxylic acid (11). A −78° C. solution of 9 (10 mg, 0.02 mmol) in THF (0.4 mL) was treated with tert-BuLi (60 µL, 0.01 mmol, 1.7 M/pentane). After 30 min., 2 mL saturated NH₄Cl solution was added and the resulting mixture was extracted with dichloromethane (3×20 mL). The combined dichloromethane solution was dried (Na₂SO₄), filtered and evaporated. The crude product still contained vinyl bromide 9 and so was resubmitted to the reaction conditions: THF (0.2 mL) and tert-BuLi (100 mL,) were added and the reaction was stirred for 3 h at −40° C. and then worked up as above. Purification by flash chromatography on silica gel (0%→30% MeOH/CH₂Cl₂) gave compound 11 (4 mg, 0.01 mmol, 50%).

Compounds 12a and 12b

12a. Triethylamine and ethyl chloroformate are added sequentially to a solution of compound 10 in CH₂Cl₂ at room temperature. After 2.5 h, triethylamine and ethylene glycol are added. After stirring overnight at room temperature, the reaction mixture is partitioned between H₂O and CH₂Cl₂. The phases are separated and the aqueous phase is extracted with CH₂Cl₂ (2×). The combined organic phase is washed with 1 N HCl then dried (MgSO₄), filtered and concentrated in vacuo. Purification of the residue by flash column chromatography on silica gel (10% CH₃OH/CH₂Cl₂) affords the desired compound.

12b. Triethylamine and ethyl chloroformate are added sequentially to a solution of compound 10 in CH₂Cl₂ at room temperature. After 2.5 h, triethylamine and 4-(2-hydroxy-ethyl)-morphine are added. After stirring overnight at room temperature, the reaction mixture is partitioned between H₂O and CH₂Cl₂. The phases are separated and the aqueous phase is extracted with CH₂Cl₂ (2×). The combined organic phase is washed with 1 N HCl then dried (MgSO₄), filtered and concentrated in vacuo. Purification of the residue by flash column chromatography on silica gel (10% CH₃OH/CH₂Cl₂) affords the desired compound the desired compound.

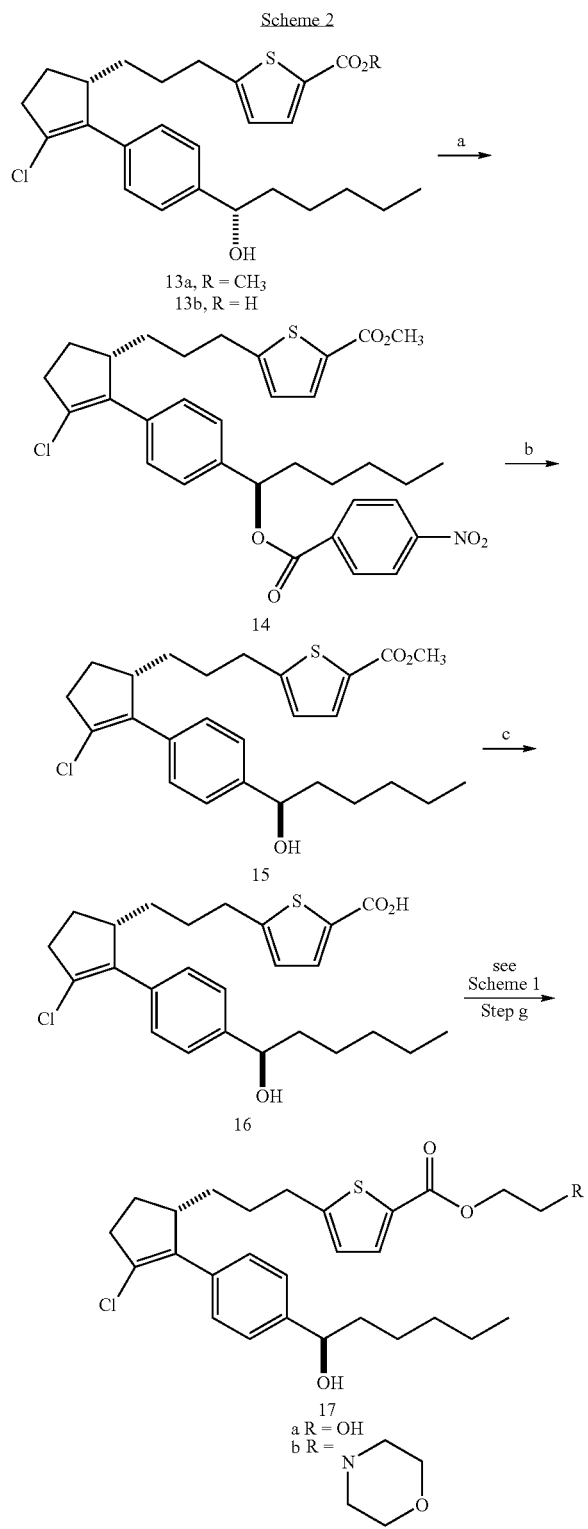

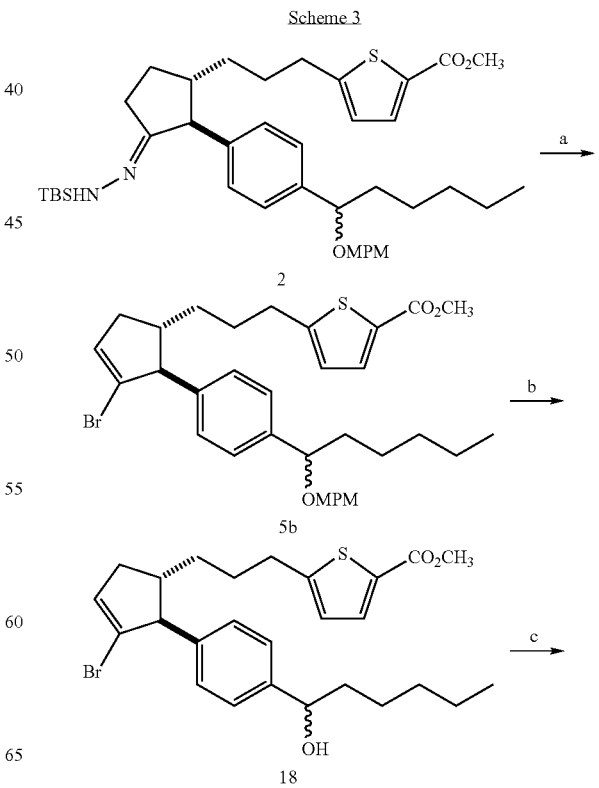

Conditions: (a) 4-nitrobenzoic acid, DIAD, PPh₃, THF; (b) aq. NaOH, MeOH; (c) aq. LiOH, THF 60° C.

5-(3-{(S)-3-Chloro-2-[4-((S)-1-hydroxy-hexyl)-phenyl]-cyclopent-2-enyl}-propyl)-thiophene-2-carboxylic acid and the corresponding methyl ester (13a,b). Compounds 13a and 13b were prepared as described for the diastereomer mixture in scheme 1 and U.S. 60/746,386, ultimately starting from the enantiomerically pure (S)-1-(4-Bromo-phenyl)-hexan-1-ol (WO 2005/061449 A1).

5-[3-((S)-3-Chloro-2-{4-[(R)-1-(4-nitro-benzoyloxy)-hexyl]-phenyl}-cyclopent-2-enyl)-propyl]-thiophene-2-carboxylic acid methyl ester (14). A solution of diisopropyl azodicarboxylate (25 mL, 0.13 mmol) in THF (1 mL) was added to an ice cold solution of the alcohol (13a, 24 mg, 0.052 mmol), 4-nitrobenzoic acid (26 mg, 0.15 mmol), and Ph₃P (34 mg, 0.13 mmol) in THF (1 mL). The solution was allowed to warm to room temperature and after 1.5 h, saturated NaHCO₃ solution (15 mL) was added. The resulting mixture was extracted with ethyl acetate (2×20 mL) and the combined ethyl acetate solution was dried (MgSO₄), filtered and evaporated. Purification by flash chromatography on silica gel (0%→40% ethyl acetate/hexanes) gave compound 14 (18 mg, 0.03 mmol, 57%).

5-(3-{(S)-3-Chloro-2-[4-((R)-1-hydroxy-hexyl)-phenyl]-cyclopent-2-enyl}-propyl)-thiophene-2-carboxylic acid methyl ester (15). A solution of 5% NaOH/MeOH (0.25 mL, 0.31 mmol), ester 14 (18 mg, 0.029 mmol) and THF (0.05 mL) was allowed to stir at room temperature. After 30 min., 10 mL 1 M HCl solution was added and the resulting mixture was extracted with ethyl acetate (2×20 mL). The combined ethyl acetate solution was dried (MgSO₄), filtered and evaporated. Purification by flash chromatography on silica gel (0%→50% ethyl acetate/hexanes) gave compound 15 (11 mg, 0.024 mmol, 82%).

5-(3-{(S)-3-Chloro-2-[4-((R)-1-hydroxy-hexyl)-phenyl]-cyclopent-2-enyl}-propyl)-thiophene-2-carboxylic acid (16). The previously described LiOH procedure (U.S. Pat. No. 7,091,231) was used at 60° C. overnight.

Compounds 17a and 17b are produced according to the procedures described in Scheme 1, Step g.

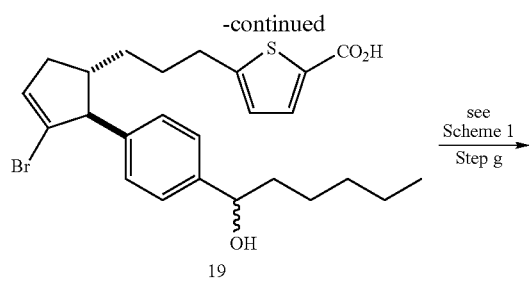

19

Scheme 4

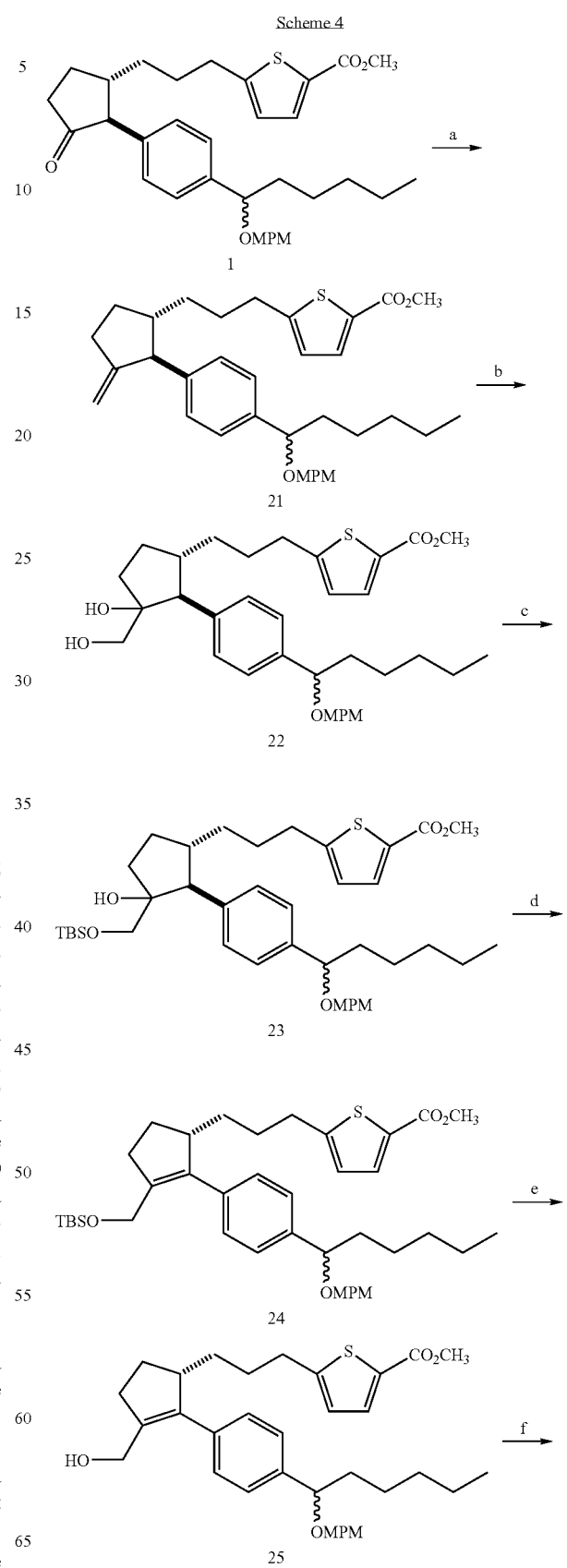

20
a R = OH
b R = (morpholine)

Conditions: (a) Br₂, 2-t-Butyl-1,1,3,3-tetramethylguanidine, CH₂Cl₂ -78° C.; (b) DDQ, CH₂Cl₂/H₂O; (c) 1 M LiOH, THF 60° C.

5-[3-((1S,2S)-3-Bromo-2-{4-[1-(4-methoxy-benzyloxy)-hexyl]-phenyl}-cyclopent-3-enyl)-propyl]-thiophene-2-carboxylic acid methyl ester (5b, scheme 3). Br₂ (70 μL, 1.36 mmol) was added dropwise to a −78° C. solution of BTMG (600 μL) in dichloromethane (1.8 mL). The resulting colorless solution was warmed to room temperature and was stirred for 15 min. A solution of hydrazone 2 (prepared from 0.17 mmol of ketone 1) in dichloromethane (1 mL) was added, rinsing with 1 mL dichloromethane. After 1 h at room temperature, the reaction was cooled to 0° C. and more Br₂ (70 μL, 1.36 mmol) was added. The reaction was allowed to warm to room temperature, was stirred overnight and then was quenched by addition of saturated NH₄Cl solution. The resulting mixture was extracted with dichloromethane (3×20 mL) and the combined dichloromethane solution was washed with brine and then was dried (Na₂SO₄), filtered and evaporated. Purification by flash chromatography on silica gel (0%→50% ethyl acetate/hexanes) provided compound 5a (51 mg, 50%).

5-(3-{(1S,2S)-3-Bromo-2-[4-(1-hydroxy-hexyl)-phenyl]-cyclopent-3-enyl}-propyl)-thiophene-2-carboxylic acid methyl ester (18). The previously described DDQ procedure was used (U.S. Pat. No. 7,091,231).

5-(3-{(1S,2S)-3-Bromo-2-[4-(1-hydroxy-hexyl)-phenyl]-cyclopent-3-enyl}-propyl)-thiophene-2-carboxylic acid (19). The previously described LiOH procedure was used at 60° C. overnight (U.S. Pat. No. 7,091,231).

Compounds 20a and 20b are produced according to the procedures described in Scheme 1, Step g.

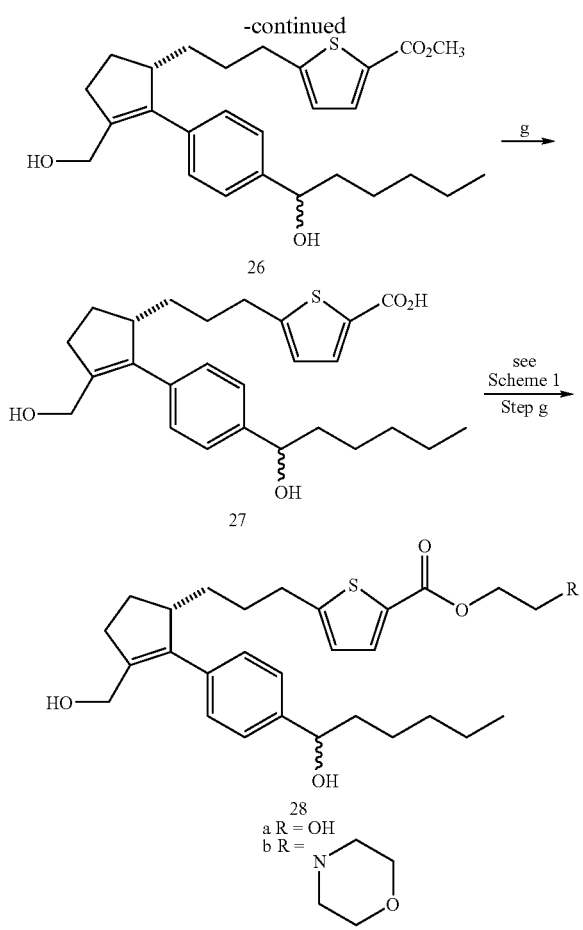

Conditions: (a) Tebbe reagent, toluene; (b) OsO4, NMO, acetone; (c) TBSOTf, 2,6-lutidine, ClCH2CH2Cl; (d) Methyl N-(triethylammoniumsulphonyl)carbamate (Burgess reagent), PhH 50° C.; (e) HF•pyridine, CH3CN 0° C.; (f) DDQ, H2O/CH2Cl2; (g) 1 M LiOH, THF 60° C.

5-[3-((1S,2R)-2-{4-[1-(4-Methoxy-benzyloxy)-hexyl]-phenyl}-3-methylene-cyclopentyl)-propyl]-thiophene-2-carboxylic acid methyl ester (21). A solution of ketone 1 (143 mg, 0.25 mmol) in toluene (1.2 mL) was cannula transferred to an ice-cold solution of the Tebbe reagent-bis(cyclopentadienyl)-μ-chloro(dimethylaluminum)-μ-methylenetitanium (1.6 mL, 0.80 mmol, 0.5 M/toluene) in 1.2 mL toluene, rinsing with 1.2 mL toluene. The reaction was allowed to warm to room temperature and after 1 h was quenched by addition of 0.2 mL 6 M NaOH (0° C.). The resulting mixture was warmed to room temperature, diluted with 40 mL of dichloromethane, and then was dried (Na2SO4), filtered and evaporated. Purification by flash chromatography (0% ethyl acetate/hexanes→100%) gave compound 21 (97 mg, 86%).

5-[3-((1S,2S)-3-Hydroxy-3-hydroxymethyl-2-{4-[1-(4-methoxy-benzyloxy)-hexyl]-phenyl}-cyclopentyl)-propyl]-thiophene-2-carboxylic acid methyl ester (22). An aqueous solution of OsO4 (0.32 mL, 0.05 mmol, 4 wt. %) was added to an ice-cold mixture of alkene 21 (59 mg, 0.10 mmol) and NMO (4-methylmorpholine N-oxide, 27 mg, 0.23 mmol) in acetone (2.2 mL). The reaction was allowed to warm to room temperature and after 1 h, 5 mL saturated NaHCO3 was added. The resulting mixture was extracted with ethyl acetate (3×30 mL), washed with brine and then was dried (Na2SO4), filtered and evaporated. Purification by flash chromatography on silica gel (0%→100% ethyl acetate/hexanes) gave compound 22 (51 mg, 82%).

5-[3-((1S,2S)-3-(tert-Butyl-dimethyl-silanyloxymethyl)-3-hydroxy-2-{4-[1-(4-methoxy-benzyloxy)-hexyl]-phenyl}-cyclopentyl)-propyl]-thiophene-2-carboxylic acid methyl ester (23). TBSOTf (16 μL, 0.070 mmol) was added to a 0° C. solution of alcohol 22 (37 mg, 0.063 mmol) and 2,6-lutidine (16 μL, 0.14 mmol) in ClCH2CH2Cl (0.5 mL). The reaction was allowed to warm to room temperature and after 2 h, saturated NaHCO3 solution was added. The resulting mixture was extracted with dichloromethane (3×20 mL) and the combined dichloromethane solution was washed with brine and then was dried (Na2SO4), filtered and evaporated. Purification by flash chromatography on silica gel (ethyl acetate/hexanes) provided compound 23 (39 mg, 87%).

5-[3-((S)-3-(tert-Butyl-dimethyl-silanyloxymethyl)-2-{4-[1-(4-methoxy-benzyloxy)-hexyl]-phenyl}-cyclopent-2-enyl)-propyl]-thiophene-2-carboxylic acid methyl ester (24). A solution of 23 (46 mg, 0.065 mmol) and methyl N-(triethylammoniumsulphonyl)carbamate (Burgess reagent, 62 mg, 0.26 mmol) in benzene (0.9 mL) was heated at 50° C. After 1 h, the reaction was quenched by addition of H2O and the resulting mixture was extracted with dichloromethane (3×20 mL). The combined organic solution was washed with brine and then was dried (Na2SO4), filtered and evaporated. Purification by flash chromatography on silica gel (ethyl acetate/hexanes) gave compound 24 (31 mg, 68%).

5-[3-((S)-3-Hydroxymethyl-2-{4-[1-(4-methoxy-benzyloxy)-hexyl]-phenyl}-cyclopent-2-enyl)-propyl]-thiophene-2-carboxylic acid methyl ester (25). The previously described HF•pyridine procedure was used (U.S. Pat. No. 7,091,231).

5-(3-{(S)-2-[4-(1-Hydroxy-hexyl)-phenyl]-3-hydroxymethyl-cyclopent-2-enyl}-propyl)-thiophene-2-carboxylic acid methyl ester (26). The previously described DDQ procedure was used (U.S. Pat. No. 7,091,231).

5-(3-{(S)-2-[4-(1-Hydroxy-hexyl)-phenyl]-3-hydroxymethyl-cyclopent-2-enyl}-propyl)-thiophene-2-carboxylic acid (27). The previously described LiOH procedure was used at 60° C. overnight (U.S. Pat. No. 7,091,231).

Compounds 28a and 28b are produced according to the procedures described in Scheme 1, Step g.

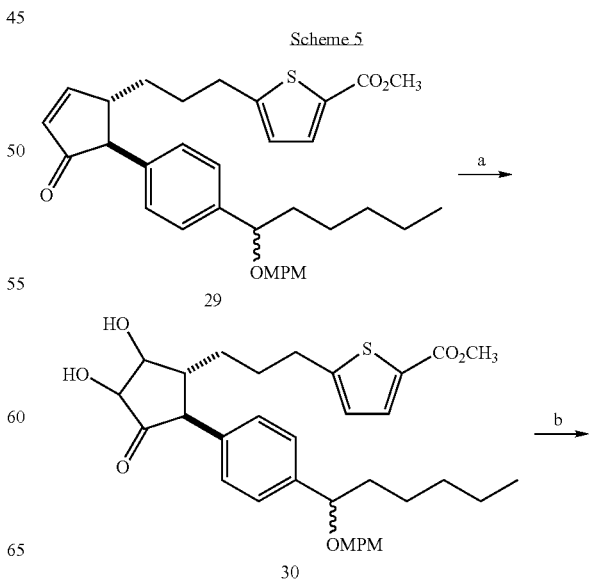

-continued

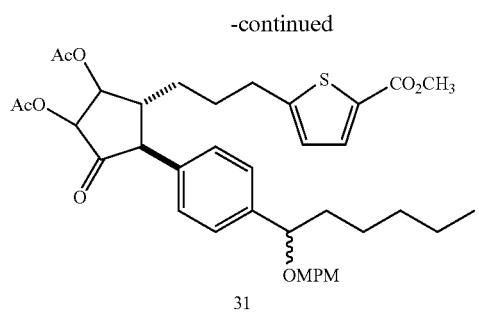

31

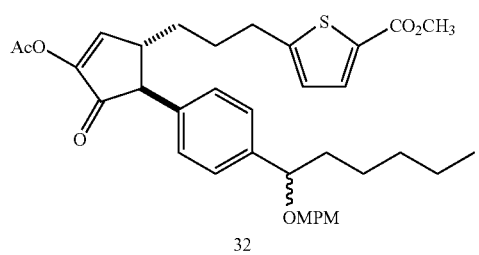

32

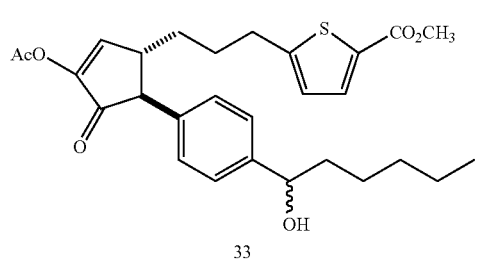

33

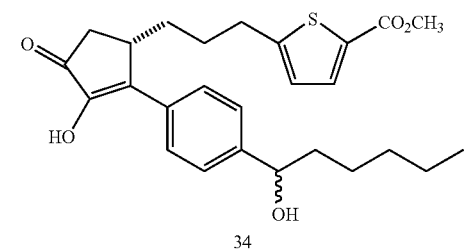

34

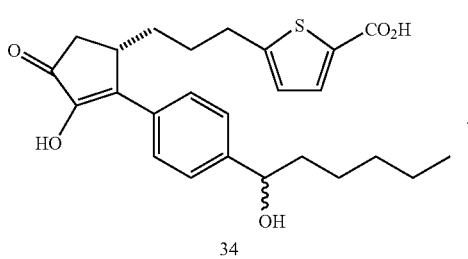

34

-continued

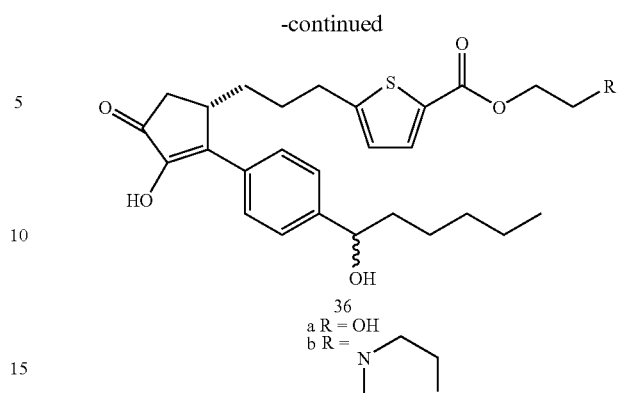

36
a R = OH
b R = [morpholine]

Conditions: (a) OsO₄, NMO, acetone; (b) Ac₂O, Et₃N, DMAP, ClCH₂CH₂Cl; (c) DBU, ether; (d) DDQ, H₂O/CH₂Cl₂; (e) K₂CO₃, MeOH; (f) rabbit liver esterase, pH 7.2 phosphate buffer, DMSO.

5-[3-((1R,5S)-2,3-Dihydroxy-5-{4-[1-(4-methoxy-benzyloxy)-hexyl]-phenyl}-4-oxo-cyclopentyl)-propyl]-thiophene-2-carboxylic acid methyl ester (30). A solution of OsO₄ (220 µL, 0.036 mmol, 4 wt %/H₂O) was added dropwise to a 0° C. mixture of 5-[3-((1S,5S)-5-{4-[1-(4-Methoxy-benzyloxy)-hexyl]-phenyl}-4-oxo-cyclopent-2-enyl)-propyl]-thiophene-2-carboxylic acid methyl ester (29) (39 mg, 0.070 mmol, see U.S. 60/746,386) and NMO (16 mg, 0.14 mmol). The reaction was allowed to warm to room temperature and after 1 h, was quenched by addition of 5% NaHSO₃ solution. The resulting mixture was extracted with ethyl acetate (3×30 mL) and the combined ethyl acetate solution was washed with brine and then was dried (Na₂SO₄), filtered and evaporated. Purification by flash chromatography on silica gel (ethyl acetate/hexanes) provided compound 30 (15 mg, 36%).

5-[3-((1R,5S)-2,3-Diacetoxy-5-{4-[1-(4-methoxy-benzyloxy)-hexyl]-phenyl}-4-oxo-cyclopentyl)-propyl]-thiophene-2-carboxylic acid methyl ester (31). Ac₂O (100 µL, 1.06 mmol), Et₃N (160 µL, 1.15 mmol) and DMAP (26 mg, 0.21 mmol) were added to a solution of the diol (30, 55 mg, 0.093 mmol) in ClCH₂CH₂Cl (0.5 mL). The reaction was stirred overnight, diluted with ethyl acetate and then washed with 1 M HCl, saturated NaHCO₃, and brine. The ethyl acetate solution was then dried (Na₂SO₄), filtered and evaporated. Purification by flash chromatography on silica gel (ethyl acetate/hexanes) provided compound 31 (32 mg, 51%).

5-[3-((1S,5S)-3-Acetoxy-5-{4-[1-(4-methoxy-benzyloxy)-hexyl]-phenyl}-4-oxo-cyclopent-2-enyl)-propyl]-thiophene-2-carboxylic acid methyl ester (32). DBU (15 µL, 0.10 mmol) was added to an ice-cold solution of diacetate 31 (32 mg, 0.048 mmol) in ether (0.5 mL). The solution was stirred at 0° C. for 30 min. and then was allowed to warm to room temperature. After stirring overnight, 1 M HCl was added and the resulting mixture was extracted with ethyl acetate (3×25 mL). The combined organic solution was washed with brine and then was dried (Na₂SO₄), filtered and evaporated. Purification by flash chromatography on silica gel (0%→100% ethyl acetate/hexanes) provided compound 32 (21 mg, 71%).

5-(3-{(1S,5S)-3-Acetoxy-5-[4-(1-hydroxy-hexyl)-phenyl]-4-oxo-cyclopent-2-enyl}-propyl)-thiophene-2-carboxylic acid methyl ester (33). The previously described (U.S. Pat. No. 7,091,231) DDQ procedure was used.

5-(3-{(S)-3-Hydroxy-2-[4-(1-hydroxy-hexyl)-phenyl]-4-oxo-cyclopent-2-enyl}-propyl)-thiophene-2-carboxylic acid methyl ester (34). $K_2CO_3$ (6 mg, 0.046 mmol) was added to a solution of 33 (12 mg, 0.019 mmol) in methanol (0.55 mL). After 2 h, excess saturated $NH_4Cl$ solution was added and the resulting mixture was extracted with dichloromethane (3×20 mL). The combined organic solution was dried, filtered and evaporated. Purification by flash chromatography on silica gel (ethyl acetate/hexanes) provided compound 34 (5 mg, 58%).

5-(3-{(S)-3-Hydroxy-2-[4-(1-hydroxy-hexyl)-phenyl]-4-oxo-cyclopent-2-enyl}-propyl)-thiophene-2-carboxylic acid (35). A mixture of 34 (5 mg, 0.011 mmol), rabbit liver esterase (3 mg, Aldrich), DMSO (50 μL) and pH 7.2 phosphate buffer (0.5 mL) was stirred at room temperature overnight. The reaction was diluted with $CH_2Cl_2$ and washed with $H_2O$ and brine. The resulting organic solution was dried ($Na_2SO_4$), filtered and evaporated. Purification by flash chromatography on silica gel (0%→30% methanol/dichloromethane) gave compound 35 (1 mg, 21%).

Compounds 36a and 36b are produced according to the procedures described in Scheme 1, Step g.

The following compounds are non-limiting examples of compounds that can be made according to the present description.

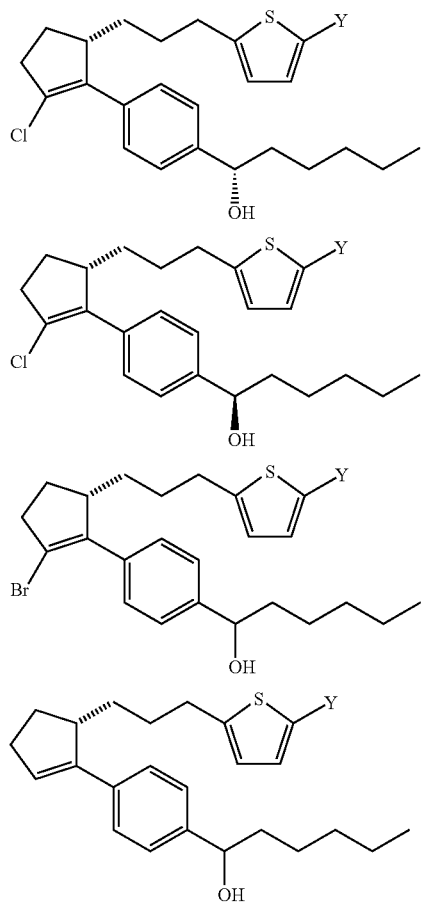

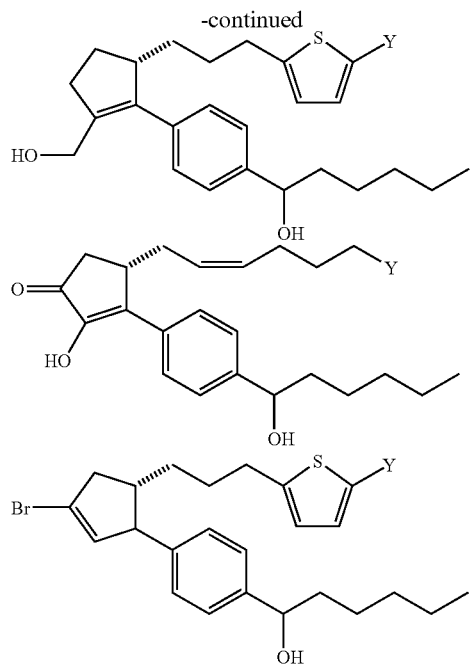

IN VIVO EXAMPLES

The following are hypothetical examples demonstrating how a person may be treated with the compounds disclosed herein.

Treatment Example 1

An aqueous liquid comprising H1 is given topically to the eye of a person suffering from elevated intraocular pressure. A few hours after administration, the person's intraocular pressure is reduced

Treatment Example 2

An aqueous liquid comprising H2 is given topically to the eye of a person suffering from elevated intraocular pressure. A few hours after administration, the person's intraocular pressure is reduced

Treatment Example 3

An aqueous liquid comprising H3 is given topically to the eye of a person suffering from elevated intraocular pressure. A few hours after administration, the person's intraocular pressure is reduced.

Treatment Example 4

An aqueous liquid comprising H4 is given topically to the eye of a person suffering from elevated intraocular pressure. A few hours after administration, the person's intraocular pressure is reduced

Treatment Example 5

An aqueous liquid comprising H5 is given topically to the eye of a person suffering from elevated intraocular pressure. A few hours after administration, the person's intraocular pressure is reduced.

Treatment Example 6

An aqueous liquid comprising H6 is given topically to the eye of a person suffering from elevated intraocular pressure. A few hours after administration, the person's intraocular pressure is reduced.

Treatment Example 7

An aqueous liquid comprising H7 is given topically to the eye of a person suffering from elevated intraocular pressure. A few hours after administration, the person's intraocular pressure is reduced

Treatment Example 8

An aqueous liquid comprising H8 is given topically to the eye of a person suffering from elevated intraocular pressure. A few hours after administration, the person's intraocular pressure is reduced.

H1
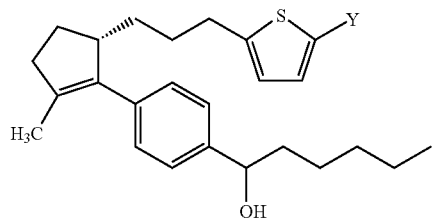

H2
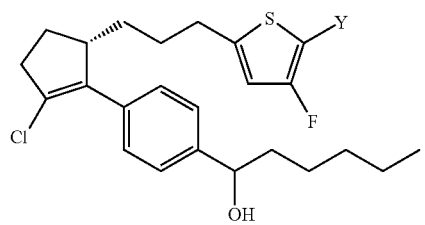

H3
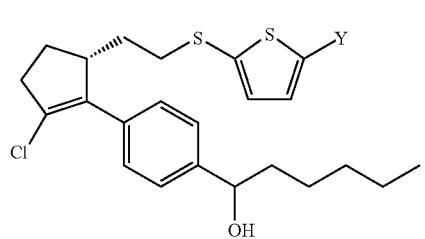

H4
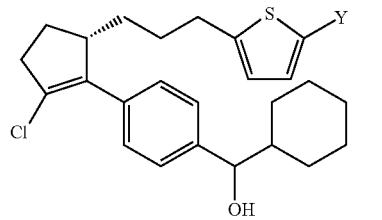

-continued

H5
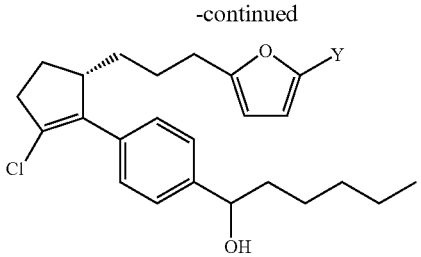

H6
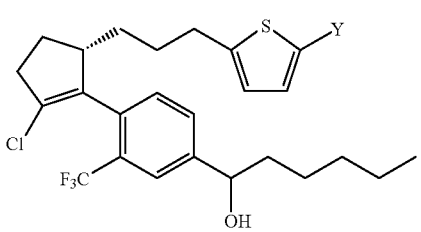

H7
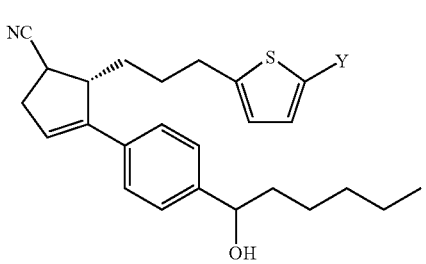

H8
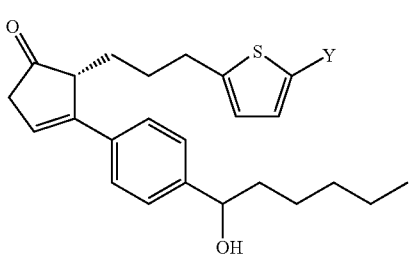

Treatment Example 9

An aqueous liquid comprising H9 is given topically to the eye of a person suffering from elevated intraocular pressure. A few hours after administration, the person's intraocular pressure is reduced.

Treatment Example 10

An aqueous liquid comprising H10 is given topically to the eye of a person suffering from elevated intraocular pressure. A few hours after administration, the person's intraocular pressure is reduced.

Treatment Example 11

An aqueous liquid comprising H11 is given topically to the eye of a person suffering from elevated intraocular pressure. A few hours after administration, the person's intraocular pressure is reduced.

Treatment Example 12

An aqueous liquid comprising H12 is given topically to the eye of a person suffering from elevated intraocular pressure. A few hours after administration, the person's intraocular pressure is reduced.

Treatment Example 13

An aqueous liquid comprising H13 is given topically to the eye of a person suffering from elevated intraocular pressure. A few hours after administration, the person's intraocular pressure is reduced.

Treatment Example 14

An aqueous liquid comprising H14 is given topically to the eye of a person suffering from elevated intraocular pressure. A few hours after administration, the person's intraocular pressure is reduced.

Treatment Example 15

An aqueous liquid comprising H15 is given topically to the eye of a person suffering from elevated intraocular pressure. A few hours after administration, the person's intraocular pressure is reduced.

Treatment Example 16

An aqueous liquid comprising H16 is given topically to the eye of a person suffering from elevated intraocular pressure. A few hours after administration, the person's intraocular pressure is reduced.

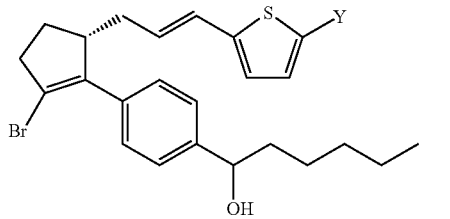

H9

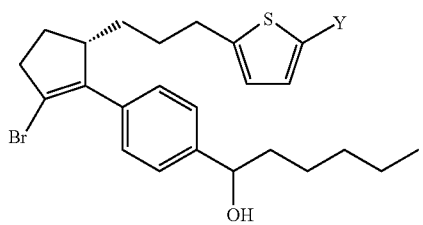

H10

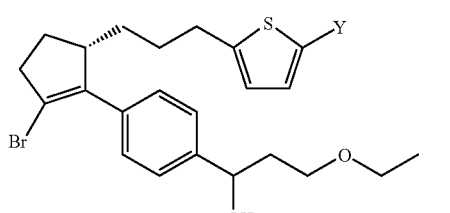

H11

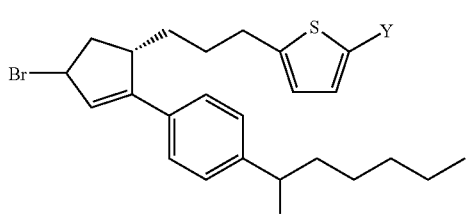

H12

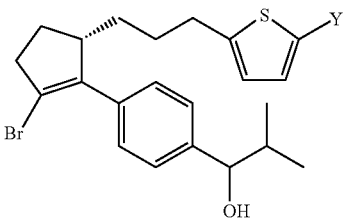

H13

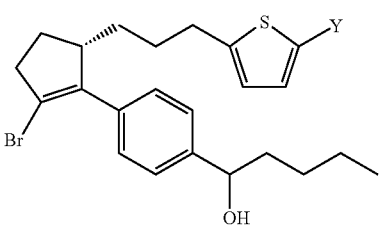

H14

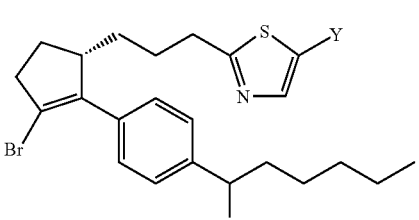

H15

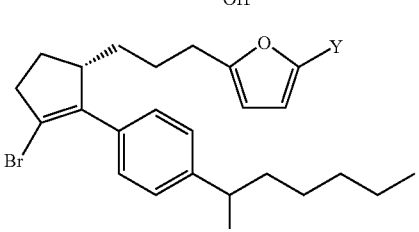

H16

Treatment Example 17

An aqueous liquid comprising H17 is given topically to the eye of a person suffering from elevated intraocular pressure. A few hours after administration, the person's intraocular pressure is reduced.

Treatment Example 18

An aqueous liquid comprising H18 is given topically to the eye of a person suffering from elevated intraocular pressure. A few hours after administration, the person's intraocular pressure is reduced.

Treatment Example 19

An aqueous liquid comprising H19 is given topically to the eye of a person suffering from elevated intraocular pressure. A few hours after administration, the person's intraocular pressure is reduced

Treatment Example 20

An aqueous liquid comprising H20 is given topically to the eye of a person suffering from elevated intraocular pressure. A few hours after administration, the person's intraocular pressure is reduced.

Treatment Example 21

An aqueous liquid comprising H21 is given topically to the eye of a person suffering from elevated intraocular pressure. A few hours after administration, the person's intraocular pressure is reduced.

Treatment Example 22

An aqueous liquid comprising H22 is given topically to the eye of a person suffering from elevated intraocular pressure. A few hours after administration, the person's intraocular pressure is reduced

Treatment Example 23

An aqueous liquid comprising H23 is given topically to the eye of a person suffering from elevated intraocular pressure. A few hours after administration, the person's intraocular pressure is reduced.

Treatment Example 24

An aqueous liquid comprising H24 is given topically to the eye of a person suffering from elevated intraocular pressure. A few hours after administration, the person's intraocular pressure is reduced.

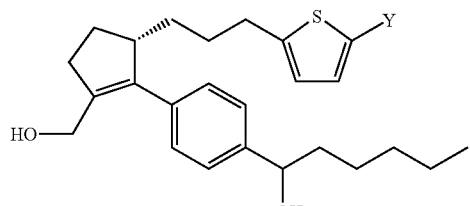
H17

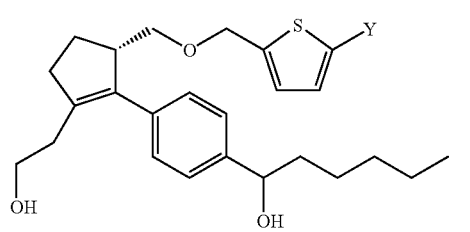
H18

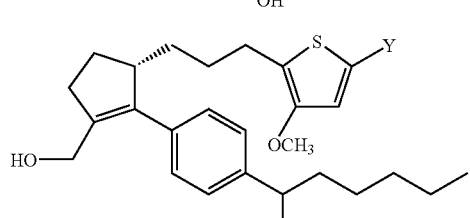
H19

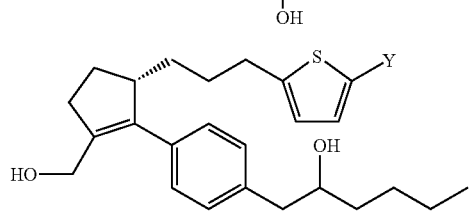
H20

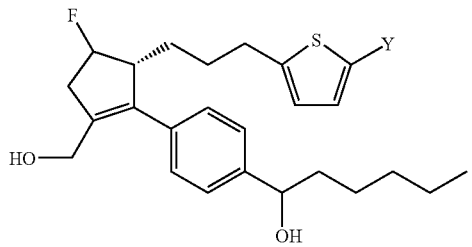
H21

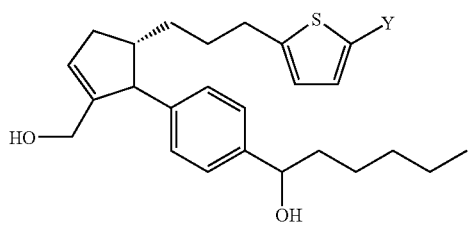
H22

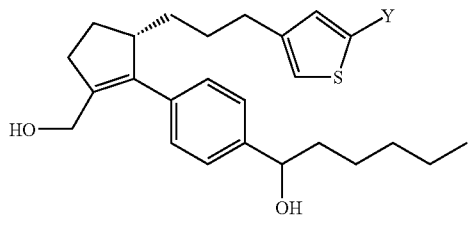
H23

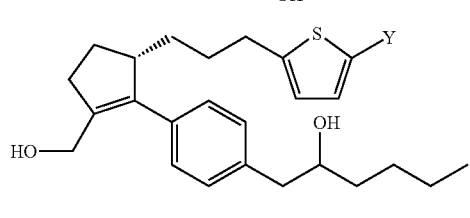
H24

Treatment Example 25

An aqueous liquid comprising H25 is given topically to the eye of a person suffering from elevated intraocular pressure. A few hours after administration, the person's intraocular pressure is reduced.

Treatment Example 26

An aqueous liquid comprising H26 is given topically to the eye of a person suffering from elevated intraocular pressure. A few hours after administration, the person's intraocular pressure is reduced.

Treatment Example 27

An aqueous liquid comprising H27 is given topically to the eye of a person suffering from elevated intraocular pressure. A few hours after administration, the person's intraocular pressure is reduced.

Treatment Example 28

An aqueous liquid comprising H28 is given topically to the eye of a person suffering from elevated intraocular pressure. A few hours after administration, the person's intraocular pressure is reduced.

Treatment Example 29

An aqueous liquid comprising H29 is given topically to the eye of a person suffering from elevated intraocular pressure. A few hours after administration, the person's intraocular pressure is reduced.

Treatment Example 30

An aqueous liquid comprising H30 is given topically to the eye of a person suffering from elevated intraocular pressure. A few hours after administration, the person's intraocular pressure is reduced.

Treatment Example 31

An aqueous liquid comprising H31 is given topically to the eye of a person suffering from elevated intraocular pressure. A few hours after administration, the person's intraocular pressure is reduced.

Treatment Example 32

An aqueous liquid comprising H32 is given topically to the eye of a person suffering from elevated intraocular pressure. A few hours after administration, the person's intraocular pressure is reduced.

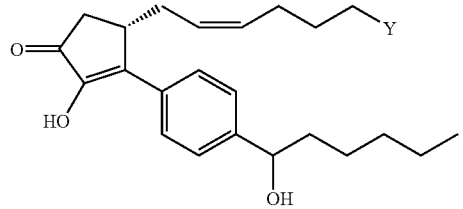
H25

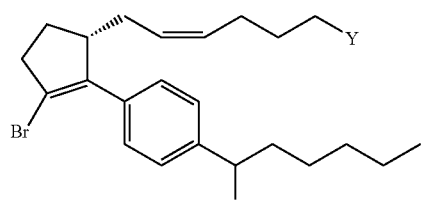
H26

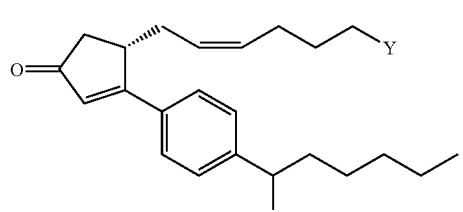
H27

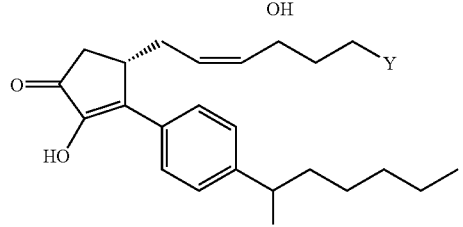
H28

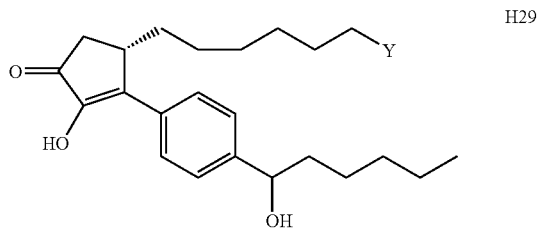
H29

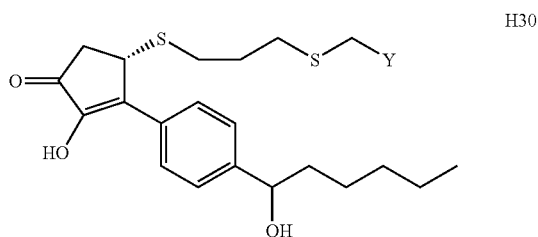
H30

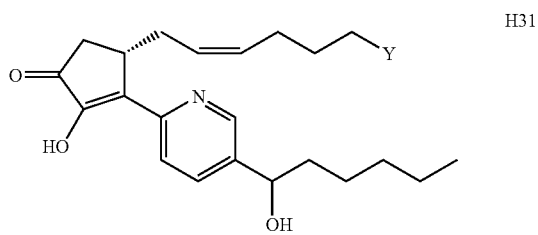
H31

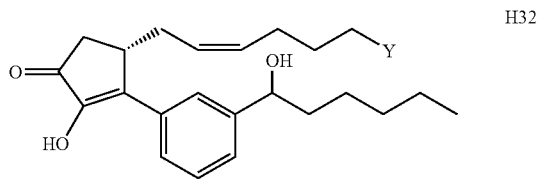
H32

Treatment Example 33

An aqueous liquid comprising H33 is given topically to the eye of a person suffering from elevated intraocular pressure. A few hours after administration, the person's intraocular pressure is reduced

Treatment Example 34

An aqueous liquid comprising H34 is given topically to the eye of a person suffering from elevated intraocular pressure. A few hours after administration, the person's intraocular pressure is reduced.

Treatment Example 35

An aqueous liquid comprising H35 is given topically to the eye of a person suffering from elevated intraocular pressure. A few hours after administration, the person's intraocular pressure is reduced.

Treatment Example 36

An aqueous liquid comprising H36 is given topically to the eye of a person suffering from elevated intraocular pressure. A few hours after administration, the person's intraocular pressure is reduced.

Treatment Example 37

An aqueous liquid comprising H37 is given topically to the eye of a person suffering from elevated intraocular pressure. A few hours after administration, the person's intraocular pressure is reduced.

Treatment Example 38

An aqueous liquid comprising H38 is given topically to the eye of a person suffering from elevated intraocular pressure. A few hours after administration, the person's intraocular pressure is reduced.

Treatment Example 39

An aqueous liquid comprising H39 is given topically to the eye of a person suffering from elevated intraocular pressure. A few hours after administration, the person's intraocular pressure is reduced.

Treatment Example 40

An aqueous liquid comprising H40 is given topically to the eye of a person suffering from elevated intraocular pressure. A few hours after administration, the person's intraocular pressure is reduced.

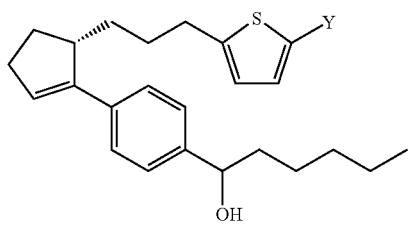

H33

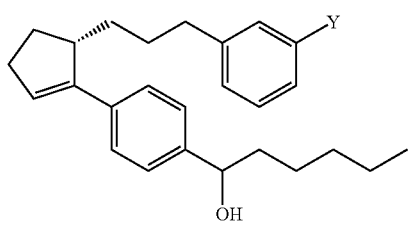

H34

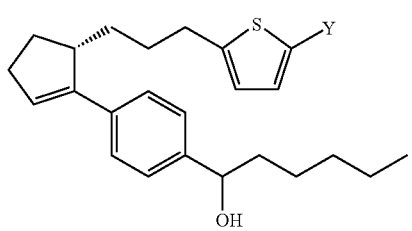

H35

-continued

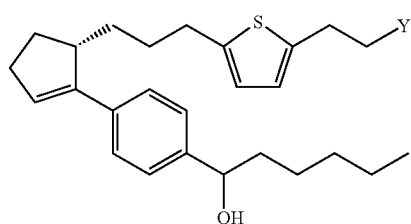

H36

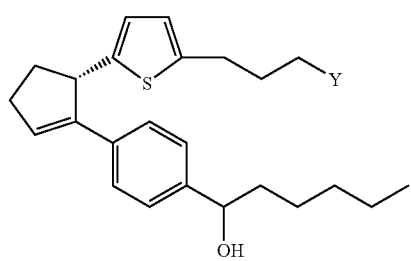

H37

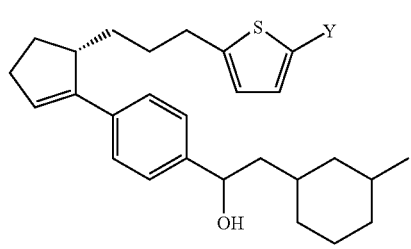

H38

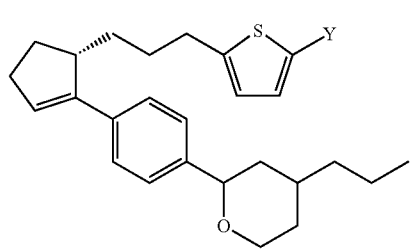

H39

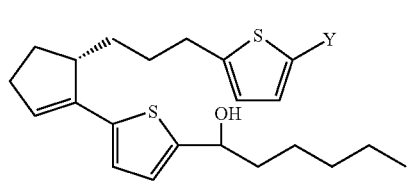

H40

Treatment Example 41

An aqueous liquid comprising H41 is given topically to the eye of a person suffering from elevated intraocular pressure. A few hours after administration, the person's intraocular pressure is reduced.

Treatment Example 42

An aqueous liquid comprising H42 is given topically to the eye of a person suffering from elevated intraocular pressure. A few hours after administration, the person's intraocular pressure is reduced.

Treatment Example 43

An aqueous liquid comprising H43 is given topically to the eye of a person suffering from elevated intraocular pressure. A few hours after administration, the person's intraocular pressure is reduced.

Treatment Example 44

An aqueous liquid comprising H44 is given topically to the eye of a person suffering from elevated intraocular pressure. A few hours after administration, the person's intraocular pressure is reduced.

Treatment Example 45

An aqueous liquid comprising H45 is given topically to the eye of a person suffering from elevated intraocular pressure. A few hours after administration, the person's intraocular pressure is reduced.

Treatment Example 46

An aqueous liquid comprising H46 is given topically to the eye of a person suffering from elevated intraocular pressure. A few hours after administration, the person's intraocular pressure is reduced.

Treatment Example 47

An aqueous liquid comprising H47 is given topically to the eye of a person suffering from elevated intraocular pressure. A few hours after administration, the person's intraocular pressure is reduced.

Treatment Example 48

An aqueous liquid comprising H48 is given topically to the eye of a person suffering from elevated intraocular pressure. A few hours after administration, the person's intraocular pressure is reduced.

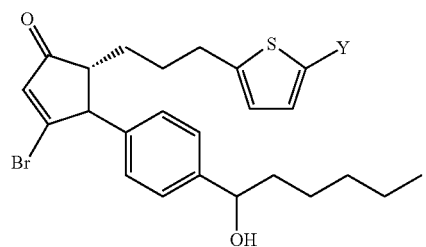

H41

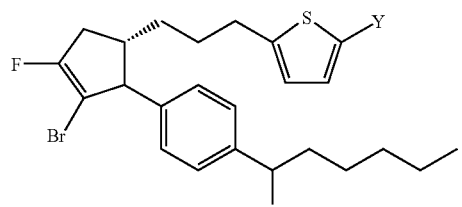

H42

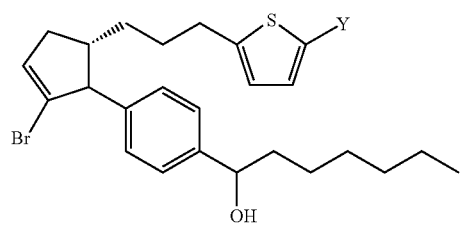

H43

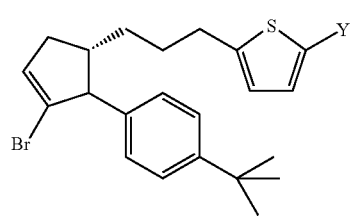

H44

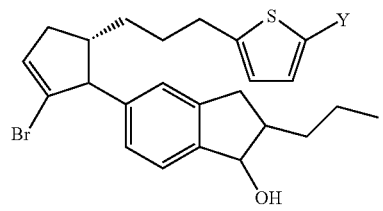

H45

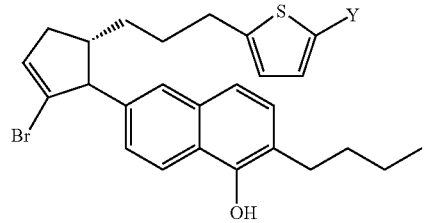

H46

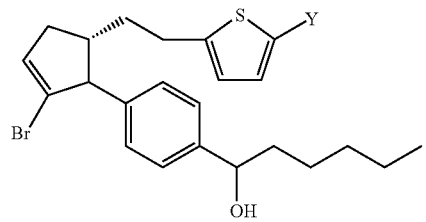

H47

-continued

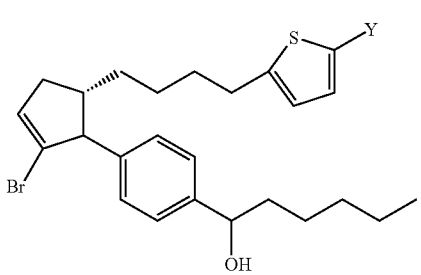
H48

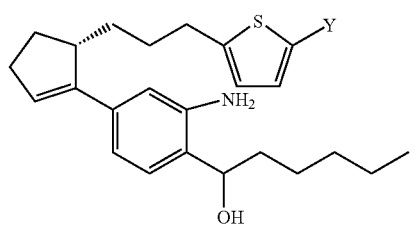
H49

Treatment Example 49

An aqueous liquid comprising H49 is given topically to the eye of a person suffering from elevated intraocular pressure. A few hours after administration, the person's intraocular pressure is reduced.

Treatment Example 50

An aqueous liquid comprising H50 is given topically to the eye of a person suffering from elevated intraocular pressure. A few hours after administration, the person's intraocular pressure is reduced.

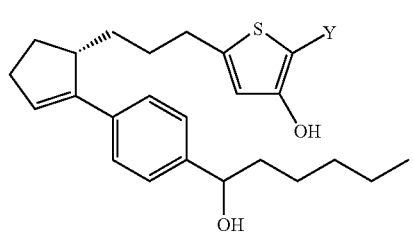
H50

Treatment Example 51

An aqueous liquid comprising H51 is given topically to the eye of a person suffering from elevated intraocular pressure. A few hours after administration, the person's intraocular pressure is reduced.

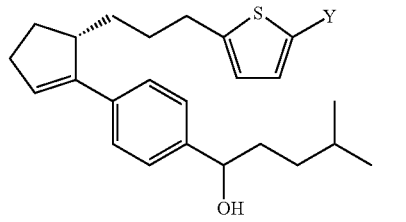
H51

Treatment Example 52

An aqueous liquid comprising H52 is given topically to the eye of a person suffering from elevated intraocular pressure. A few hours after administration, the person's intraocular pressure is reduced.

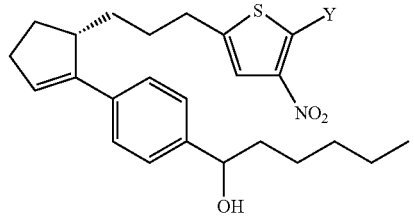
H52

Treatment Example 53

An aqueous liquid comprising H53 is given topically to the eye of a person suffering from elevated intraocular pressure. A few hours after administration, the person's intraocular pressure is reduced.

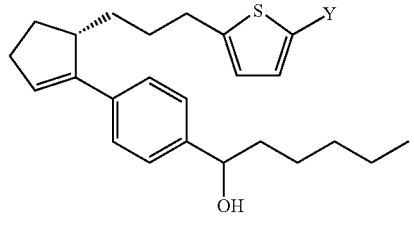
H53

Treatment Example 54

An aqueous liquid comprising H54 is given topically to the eye of a person suffering from elevated intraocular pressure. A few hours after administration, the person's intraocular pressure is reduced.

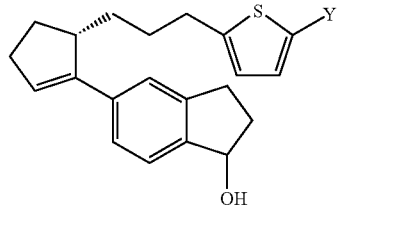
H54

Treatment Example 55

An aqueous liquid comprising H55 is given topically to the eye of a person suffering from elevated intraocular pressure. A few hours after administration, the person's intraocular pressure is reduced.

Treatment Example 56

An aqueous liquid comprising H56 is given topically to the eye of a person suffering from elevated intraocular pressure. A few hours after administration, the person's intraocular pressure is reduced.

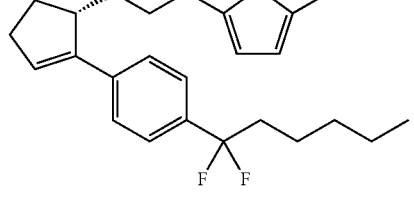
H55

-continued

H56

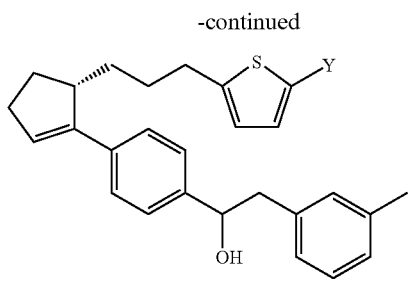

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the claims.

What is claimed is:

1. A compound of the formula

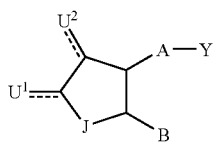

or a pharmaceutically acceptable salt thereof;
wherein a dashed line represents the presence or absence of a bond;
Y is

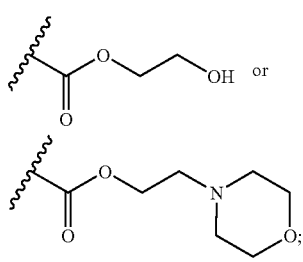

A is —$(CH_2)_6$—, cis —$CH_2CH$=$CH$—$(CH_2)_3$—, or —$CH_2C$≡$C$—$(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein 1 —$CH_2$— may be replaced by S or O, and 1 —$CH_2$—$CH_2$— may be replaced by —$CH$=$CH$— or $C$≡$C$—;

$U^1$ and $U^2$ are independently H, O; OH, I, Br, Cl, F, $CF_3$, CN, or $CH_2OH$;

J is

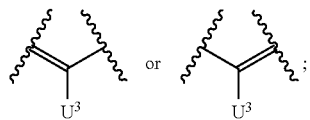

$U^3$ is H, OH, I, Br, Cl, F, CN, $C_{1-6}$ alkyl, aryl, heteroaryl, or $C_{1-6}$ hydroxyalkyl; and B is aryl or heteroaryl.

2. The compound of claim 1 where A has a structure selected from:

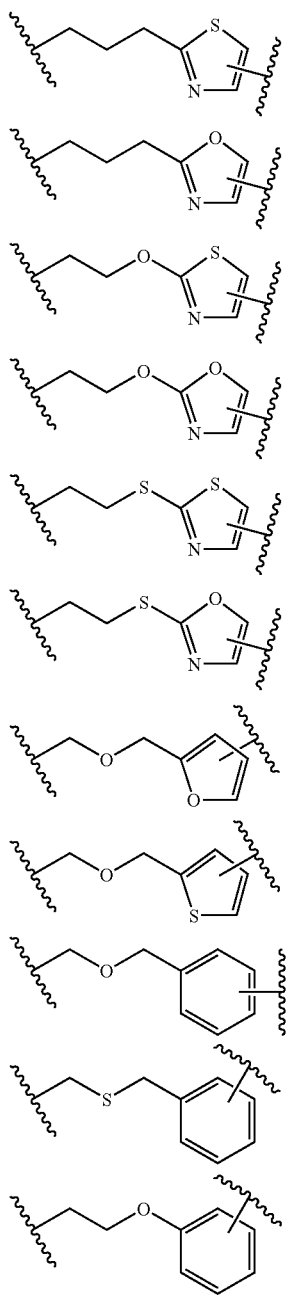

-continued

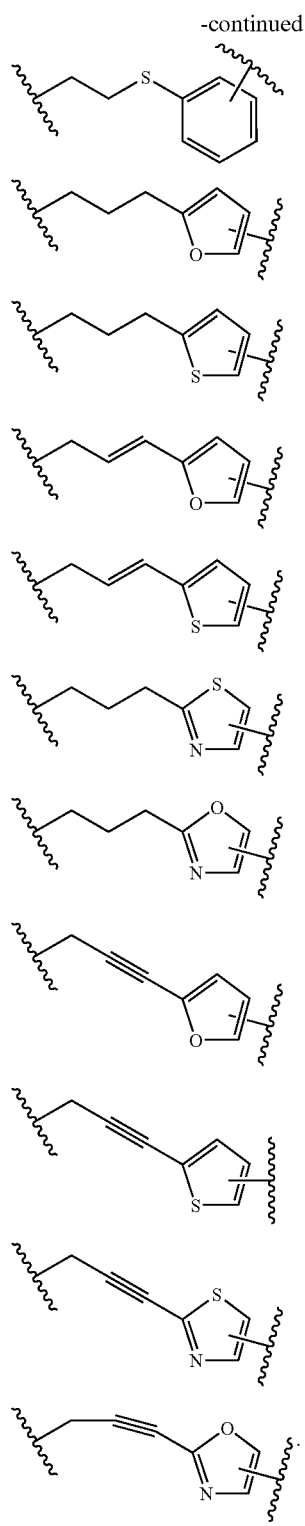

3. The compound of claim 2 wherein A is 5-(3-propyl)thiophen-2-yl.
4. The compound of claim 1 wherein A is 6-hexyl.
5. The compound of claim 1 wherein A is (Z)-6-hex-4-enyl.
6. The compound of claim 1 wherein B is a substituted phenyl.

7. The compound of claim 1 having a structure

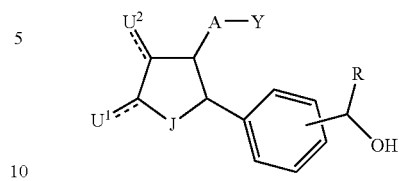

or a pharmaceutically acceptable salt thereof;
wherein R is hydrogen or $C_{1-10}$ hydrocarbyl.

8. The compound of claim 6 having a structure

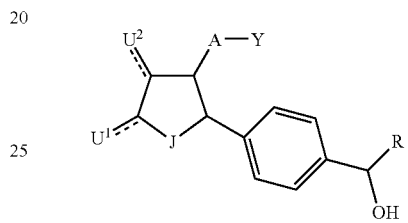

or a pharmaceutically acceptable salt thereof;
wherein R is hydrogen or $C_{1-10}$ hydrocarbyl.

9. The compound of claim 1 having a structure

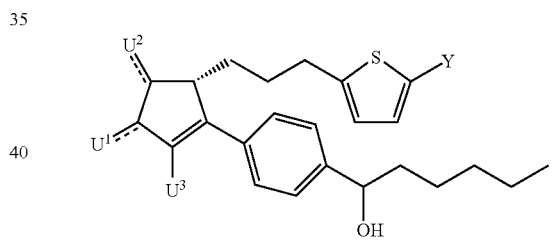

or a pharmaceutically acceptable salt thereof.

10. The compound of claim 1 having a structure

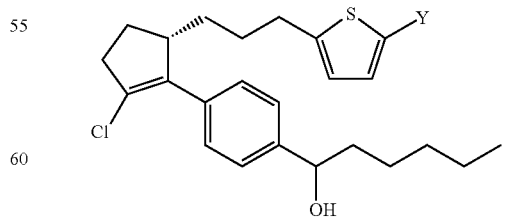

or a pharmaceutically acceptable salt thereof.

11. The compound of claim 1 having a structure
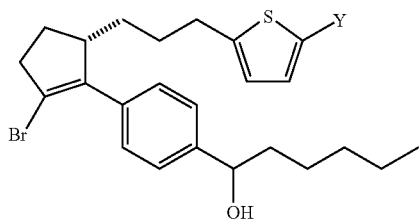
or a pharmaceutically acceptable salt thereof.
12. The compound of claim 1 having a structure
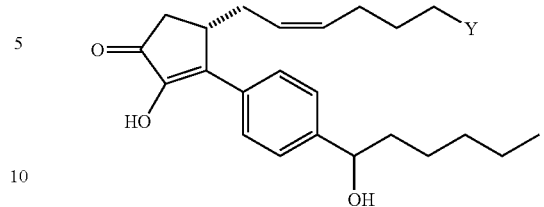
or a pharmaceutically acceptable salt thereof.
* * * * *

UNITED STATES PATENT AND TRADEMARK OFFICE
CERTIFICATE OF CORRECTION

| | | |
|---|---|---|
| PATENT NO. | : 7,713,968 B2 | Page 1 of 1 |
| APPLICATION NO. | : 12/427860 | |
| DATED | : May 11, 2010 | |
| INVENTOR(S) | : Yariv Donde et al. | |

It is certified that error appears in the above-identified patent and that said Letters Patent is hereby corrected as shown below:

On the Title page, in Item (56), under "Other Publications", column 2, line 9, delete "Opinon" and insert -- Opinion --, therefor.

In column 2, line 36, delete "varialoforme," and insert -- varioliforme, --, therefor.

In column 2, line 40, delete "crythematosus," and insert -- erythematosus, --, therefor.

In column 2, line 42, delete "Sjgren's" and insert -- Sjogren's --, therefor.

In column 2, line 44, delete "neohropathy," and insert -- nephropathy, --, therefor.

In column 2, line 55, delete "periodonritis," and insert -- periodontitis, --, therefor.

In column 2, line 62, delete "hyperphosphaturia," and insert -- hyperphosphatemia, --, therefor.

In column 8, line 23-24, after "NO$_2$," delete "and the like;".

In column 13, line 40, after "like" insert -- ; --.

In column 13, line 56, delete "indanolyl," and insert -- indolyl, --, therefor.

In column 14, line 32, delete "hydroxylalkyl" and insert -- hydroxyalkyl --, therefor.

In column 53, line 62, in Claim 3, delete "thiophen" and insert -- thiophene --, therefor.

Signed and Sealed this

Nineteenth Day of October, 2010

David J. Kappos
*Director of the United States Patent and Trademark Office*